(12) United States Patent
Orr et al.

(10) Patent No.: US 12,059,543 B2
(45) Date of Patent: Aug. 13, 2024

(54) INDWELLING PUMP FOR FACILITATING REMOVAL OF URINE FROM THE URINARY TRACT

(71) Applicant: Roivios Limited, Nassau (BS)

(72) Inventors: David E. Orr, Piedmont, SC (US); Jacob L. Upperco, Atlanta, GA (US); John R. Erbey, II, Milton, GA (US)

(73) Assignee: Roivios Limited, Nassau (BS)

( * ) Notice: Subject to any disclaimer, the term of this patent is extended or adjusted under 35 U.S.C. 154(b) by 777 days.

(21) Appl. No.: 16/640,210

(22) PCT Filed: Aug. 24, 2018

(86) PCT No.: PCT/IB2018/056444
§ 371 (c)(1),
(2) Date: Feb. 19, 2020

(87) PCT Pub. No.: WO2019/038730
PCT Pub. Date: Feb. 28, 2019

(65) Prior Publication Data
US 2020/0179665 A1    Jun. 11, 2020

Related U.S. Application Data

(60) Provisional application No. 62/550,259, filed on Aug. 25, 2017.

(51) Int. Cl.
*A61M 27/00*        (2006.01)

(52) U.S. Cl.
CPC ..... *A61M 27/008* (2013.01); *A61M 2027/004* (2013.01); *A61M 2205/3334* (2013.01);
(Continued)

(58) Field of Classification Search
CPC .............. A61M 27/008; A61M 27/002; A61M 2027/004; A61M 2205/3334;
(Continued)

(56) References Cited

U.S. PATENT DOCUMENTS 1,870,942 A    8/1932  Beatty
2,285,980 A    6/1942  Jeckel
(Continued)

FOREIGN PATENT DOCUMENTS

AU    2013332448 A1    4/2015
CA       1243581 A    10/1988
(Continued)

OTHER PUBLICATIONS

U.S. Pat. No. 10,307,564 / U.S. Appl. No. 15/214,955, "Ureteral and Bladder Catheters and Methods of Inducing Negative Pressure to Increase Renal Perfusion", Jun. 4, 2019 / filed Jul. 20, 2016.
(Continued)

*Primary Examiner* — Chelsea E Stinson
*Assistant Examiner* — Anh Bui
(74) *Attorney, Agent, or Firm* — The Webb Law Firm

(57) ABSTRACT

A pump assembly is provided, including a pump module configured to be positioned within an interior portion of a ureter and/or renal pelvis of a patient for providing negative pressure to the patient's ureter and/or kidney, the pump module including: a housing including a flow channel for conducting fluid, wherein the housing is configured to be positioned within the interior portion of the ureter and/the renal pelvis; and a pump element positioned within the channel to draw fluid through the channel; and a control module coupled to the pump module, the control module being configured to direct motion of the pump element to control flow rate of fluid passing through the channel, and including a housing configured to be positioned within at least one of a second interior portion of the patient's ureter, a second portion of the patient's renal pelvis, or an interior portion of a patient's bladder.

83 Claims, 13 Drawing Sheets

(52) U.S. Cl.
CPC ............... *A61M 2205/3337* (2013.01); *A61M 2205/3507* (2013.01); *A61M 2205/3553* (2013.01); *A61M 2205/8206* (2013.01); *A61M 2205/8243* (2013.01); *A61M 2210/1082* (2013.01); *A61M 2210/1085* (2013.01); *A61M 2210/1089* (2013.01)

(58) Field of Classification Search
CPC .. A61M 2205/3337; A61M 2205/3507; A61M 2205/3553; A61M 2205/8206; A61M 2205/8243; A61M 2210/1082; A61M 2210/1085; A61M 2210/1089; A61M 25/0017
See application file for complete search history.

(56) References Cited

U.S. PATENT DOCUMENTS

| | | | |
|---|---|---|---|
| 2,649,092 A | 8/1953 | Wallace | |
| 3,108,595 A | 10/1963 | Overment | |
| 3,397,699 A | 8/1968 | Kohl | |
| 3,561,431 A | 2/1971 | Pannier, Jr. | |
| 3,707,967 A | 1/1973 | Kitrilakis | |
| 3,875,941 A | 4/1975 | Adair | |
| 3,938,529 A | 2/1976 | Gibbons | |
| 3,938,530 A | 2/1976 | Santomieri | |
| 3,943,929 A | 3/1976 | Patel | |
| 4,265,243 A | 5/1981 | Taylor | |
| 4,306,557 A | 12/1981 | North | |
| 4,324,663 A | 4/1982 | Hirel et al. | |
| 4,349,029 A | 9/1982 | Mott | |
| 4,425,124 A | 1/1984 | Womack | |
| 4,437,856 A | 3/1984 | Valli | |
| 4,531,933 A | 7/1985 | Norton et al. | |
| 4,568,338 A | 2/1986 | Todd | |
| 4,571,241 A | 2/1986 | Christopher | |
| 4,575,371 A | 3/1986 | Nordqvist et al. | |
| 4,629,015 A | 12/1986 | Fried et al. | |
| 4,681,564 A | 7/1987 | Landreneau | |
| 4,710,169 A | 12/1987 | Christopher | |
| 4,738,667 A | 4/1988 | Galloway | |
| 4,813,935 A | 3/1989 | Haber et al. | |
| 4,834,724 A | 5/1989 | Geiss et al. | |
| 4,932,938 A | 6/1990 | Goldberg et al. | |
| 4,935,004 A | 6/1990 | Cruz | |
| 4,945,895 A | 8/1990 | Takai et al. | |
| 4,950,228 A | 8/1990 | Knapp, Jr. et al. | |
| 4,957,479 A | 9/1990 | Roemer | |
| 5,009,639 A | 4/1991 | Keymling | |
| 5,011,488 A | 4/1991 | Ginsburg | |
| 5,041,093 A | 8/1991 | Chu | |
| 5,044,902 A | 9/1991 | Malbec | |
| 5,059,169 A | 10/1991 | Zilber | |
| 5,078,684 A | 1/1992 | Yasuda | |
| 5,098,440 A | 3/1992 | Hillstead | |
| 5,116,309 A | 5/1992 | Coll | |
| 5,141,502 A | 8/1992 | Macaluso, Jr. | |
| 5,193,533 A | 3/1993 | Body et al. | |
| 5,256,146 A | 10/1993 | Ensminger et al. | |
| 5,370,690 A | 12/1994 | Barrett | |
| 5,401,257 A | 3/1995 | Chevalier, Jr. et al. | |
| 5,451,215 A | 9/1995 | Wolter | |
| 5,451,218 A | 9/1995 | Moore | |
| 5,505,717 A | 4/1996 | Moore | |
| 5,514,112 A | 5/1996 | Chu et al. | |
| 5,523,092 A | 6/1996 | Hanson et al. | |
| 5,536,274 A | 7/1996 | Neuss | |
| 5,540,701 A | 7/1996 | Sharkey et al. | |
| 5,554,144 A | 9/1996 | Wallace et al. | |
| 5,562,622 A | 10/1996 | Tihon | |
| 5,599,291 A | 2/1997 | Balbierz et al. | |
| 5,647,843 A | 7/1997 | Mesrobian et al. | |
| 5,662,713 A | 9/1997 | Andersen et al. | |
| 5,709,874 A | 1/1998 | Hanson et al. | |
| 5,727,555 A | 3/1998 | Chait | |
| 5,769,821 A | 6/1998 | Abrahamson et al. | |
| 5,785,641 A | 7/1998 | Davis | |
| 5,795,319 A | 8/1998 | Ali | |
| 5,865,764 A | 2/1999 | Moorhead | |
| 5,873,865 A | 2/1999 | Horzewski et al. | |
| 5,895,398 A | 4/1999 | Wensel et al. | |
| 5,902,336 A * | 5/1999 | Mishkin ................. | A61M 1/34 604/27 |
| 5,915,386 A | 6/1999 | Lloyd et al. | |
| 5,957,867 A | 9/1999 | Lloyd et al. | |
| 5,972,019 A | 10/1999 | Engelson et al. | |
| 5,989,207 A | 11/1999 | Hughes | |
| 6,066,113 A | 5/2000 | Overtoom | |
| 6,090,069 A | 7/2000 | Walker | |
| 6,111,520 A | 8/2000 | Allen et al. | |
| 6,200,485 B1 | 3/2001 | Kitaevich et al. | |
| 6,214,037 B1 | 4/2001 | Mitchell et al. | |
| 6,283,940 B1 | 9/2001 | Mulholland | |
| 6,332,892 B1 | 12/2001 | Desmond, III et al. | |
| 6,364,868 B1 | 4/2002 | Ikeguchi | |
| 6,402,736 B1 | 6/2002 | Brown et al. | |
| 6,442,415 B1 | 8/2002 | Bis et al. | |
| 6,461,346 B1 | 10/2002 | Buelna | |
| 6,478,778 B1 | 11/2002 | Jacobsen et al. | |
| 6,482,222 B1 | 11/2002 | Bruckheimer et al. | |
| 6,500,158 B1 | 12/2002 | Ikeguchi | |
| 6,558,350 B1 | 5/2003 | Hart et al. | |
| 6,569,150 B2 | 5/2003 | Teague et al. | |
| 6,620,202 B2 | 9/2003 | Bottcher et al. | |
| 6,648,863 B2 | 11/2003 | Reever | |
| 6,676,623 B2 | 1/2004 | Whitmore, III | |
| 6,685,744 B2 | 2/2004 | Gellman et al. | |
| 6,702,834 B1 | 3/2004 | Boylan et al. | |
| 6,764,519 B2 | 7/2004 | Whitmore, III | |
| 6,780,322 B1 | 8/2004 | Bissler et al. | |
| 6,837,868 B1 | 1/2005 | Fajnsztajn | |
| 7,025,753 B2 | 4/2006 | Reever | |
| 7,037,345 B2 | 5/2006 | Bottcher et al. | |
| 7,044,981 B2 | 5/2006 | Liu et al. | |
| 7,316,663 B2 | 1/2008 | Whitmore, III | |
| 7,329,226 B1 | 2/2008 | Ni et al. | |
| 7,396,366 B2 | 7/2008 | Ward | |
| 7,507,218 B2 | 3/2009 | Aliski et al. | |
| 7,550,978 B2 | 6/2009 | Joy et al. | |
| 7,603,170 B2 | 10/2009 | Hatlestad et al. | |
| 7,682,401 B2 | 3/2010 | Deal | |
| 7,722,677 B2 | 5/2010 | Ward | |
| 7,727,222 B2 | 6/2010 | Da Silva et al. | |
| 7,736,354 B2 | 6/2010 | Gelfand et al. | |
| 7,758,562 B2 | 7/2010 | Gelfand et al. | |
| 7,758,563 B2 | 7/2010 | Gelfand et al. | |
| 7,766,961 B2 | 8/2010 | Patel et al. | |
| 7,837,667 B2 | 11/2010 | Gelfand et al. | |
| 7,850,704 B2 | 12/2010 | Burnett et al. | |
| 7,857,803 B1 | 12/2010 | Salinas et al. | |
| 7,879,020 B1 | 2/2011 | Salinas et al. | |
| 7,938,817 B2 | 5/2011 | Gelfand et al. | |
| 7,972,292 B2 | 7/2011 | Behl et al. | |
| 8,007,460 B2 | 8/2011 | Gelfand et al. | |
| 8,021,307 B2 | 9/2011 | White et al. | |
| 8,075,513 B2 | 12/2011 | Rudko et al. | |
| 8,088,170 B2 | 1/2012 | Whitmore, III | |
| 8,105,317 B2 | 1/2012 | Reever et al. | |
| 8,152,786 B2 | 4/2012 | Shapland et al. | |
| 8,157,785 B2 | 4/2012 | Salinas et al. | |
| 8,177,741 B2 | 5/2012 | Hammack et al. | |
| 8,252,065 B2 | 8/2012 | Ward | |
| 8,328,877 B2 | 12/2012 | Gellman | |
| 8,444,623 B2 | 5/2013 | Gelfand et al. | |
| 8,486,010 B2 | 7/2013 | Nomura | |
| 8,512,795 B2 | 8/2013 | Dias et al. | |
| 8,568,387 B2 | 10/2013 | Paz | |
| 8,585,675 B2 | 11/2013 | Salinas et al. | |
| 8,597,260 B2 | 12/2013 | Tucker | |
| 8,597,273 B2 | 12/2013 | Salinas et al. | |
| 8,747,388 B2 | 6/2014 | Pandey et al. | |
| 8,795,305 B2 | 8/2014 | Martin et al. | |
| 8,827,924 B2 | 9/2014 | Paz et al. | |
| 8,852,289 B2 | 10/2014 | Whitmore, III | |

(56) References Cited

U.S. PATENT DOCUMENTS

| | | |
|---|---|---|
| 8,865,063 B2 | 10/2014 | Burnett |
| 8,932,320 B1 | 1/2015 | Janardhan et al. |
| 9,014,815 B2 | 4/2015 | Yang et al. |
| 9,060,888 B2 | 6/2015 | Gellman |
| 9,308,348 B2 | 4/2016 | Mulvihill et al. |
| 9,339,636 B1 * | 5/2016 | Khan ............... A61M 5/14276 |
| 9,682,220 B2 | 6/2017 | Schertiger et al. |
| 9,744,331 B2 | 8/2017 | Erbey, II et al. |
| 9,750,634 B2 | 9/2017 | Bar-Am |
| 9,788,928 B2 | 10/2017 | Forsell |
| 9,849,224 B2 | 12/2017 | Angwin et al. |
| 9,980,663 B2 | 5/2018 | Wabel et al. |
| 10,182,747 B2 | 1/2019 | Charlez et al. |
| 10,226,606 B2 | 3/2019 | Wan et al. |
| 10,307,566 B2 | 6/2019 | Bishawi |
| 10,449,329 B2 | 10/2019 | Foley et al. |
| 11,040,180 B2 | 6/2021 | Erbey, II et al. |
| 2001/0053936 A1 | 12/2001 | Whitmore, III |
| 2001/0056273 A1 | 12/2001 | Ewers |
| 2002/0022759 A1 | 2/2002 | Forsell |
| 2002/0052576 A1 | 5/2002 | Massengale |
| 2002/0062148 A1 | 5/2002 | Hart |
| 2002/0068093 A1 | 6/2002 | Trogolo et al. |
| 2002/0082547 A1 | 6/2002 | Deniega et al. |
| 2002/0085951 A1 | 7/2002 | Gelfand et al. |
| 2002/0143292 A1 | 10/2002 | Flinchbaugh |
| 2002/0143389 A1 | 10/2002 | St. Pierre |
| 2002/0177902 A1 | 11/2002 | Rioux et al. |
| 2002/0183852 A1 | 12/2002 | McWeeney |
| 2002/0183853 A1 | 12/2002 | Mitchell et al. |
| 2002/0188246 A1 | 12/2002 | Hayner et al. |
| 2002/0193667 A1 | 12/2002 | McNair |
| 2003/0009132 A1 | 1/2003 | Schwartz et al. |
| 2003/0018291 A1 | 1/2003 | Hill et al. |
| 2003/0060806 A1 | 3/2003 | Ikeguchi |
| 2003/0069534 A1 | 4/2003 | Work et al. |
| 2003/0074082 A1 | 4/2003 | Bottcher et al. |
| 2003/0109930 A1 | 6/2003 | Bluni et al. |
| 2003/0120261 A1 | 6/2003 | Gellman |
| 2003/0135147 A1 | 7/2003 | Rosenberg et al. |
| 2003/0135195 A1 | 7/2003 | Jimenez et al. |
| 2003/0144623 A1 | 7/2003 | Heath et al. |
| 2003/0153970 A1 | 8/2003 | Rao et al. |
| 2003/0171708 A1 | 9/2003 | Segura et al. |
| 2003/0176831 A1 | 9/2003 | Gellman et al. |
| 2003/0181842 A1 | 9/2003 | Gellman |
| 2003/0181887 A1 | 9/2003 | Castillo Deniega et al. |
| 2003/0191452 A1 | 10/2003 | Meglin et al. |
| 2003/0195456 A1 | 10/2003 | Robertson |
| 2003/0195537 A1 | 10/2003 | Dubrul et al. |
| 2003/0199805 A1 | 10/2003 | McWeeney |
| 2003/0216710 A1 | 11/2003 | Hurt |
| 2003/0224033 A1 | 12/2003 | Li et al. |
| 2004/0019358 A1 | 1/2004 | Kear |
| 2004/0054315 A1 | 3/2004 | Levin et al. |
| 2004/0054351 A1 | 3/2004 | Deniega et al. |
| 2004/0057037 A1 | 3/2004 | Ohishi et al. |
| 2004/0073194 A1 | 4/2004 | Olsen et al. |
| 2004/0097891 A1 | 5/2004 | Bolmsjo |
| 2004/0129616 A1 | 7/2004 | Mori et al. |
| 2004/0143209 A1 | 7/2004 | Liu et al. |
| 2004/0147871 A1 * | 7/2004 | Burnett ............... A61M 39/24 |
| | | 604/9 |
| 2004/0167415 A1 | 8/2004 | Gelfand et al. |
| 2004/0167634 A1 | 8/2004 | Atala et al. |
| 2004/0193098 A1 | 9/2004 | Wentling et al. |
| 2005/0042240 A1 | 2/2005 | Utterberg et al. |
| 2005/0049575 A1 | 3/2005 | Snell et al. |
| 2005/0049577 A1 | 3/2005 | Snell et al. |
| 2005/0101941 A1 | 5/2005 | Hakky et al. |
| 2005/0107736 A1 | 5/2005 | Landman et al. |
| 2005/0124969 A1 | 6/2005 | Fitzgerald et al. |
| 2005/0124978 A1 | 6/2005 | Kim |
| 2005/0177102 A1 | 8/2005 | Hart et al. |
| 2005/0187564 A1 | 8/2005 | Jayaraman |
| 2005/0240141 A1 | 10/2005 | Aliski et al. |
| 2005/0240280 A1 | 10/2005 | Aliski et al. |
| 2005/0256441 A1 | 11/2005 | Lotan et al. |
| 2005/0256447 A1 | 11/2005 | Richardson et al. |
| 2005/0288722 A1 | 12/2005 | Eigler et al. |
| 2006/0015015 A1 | 1/2006 | Kawamoto et al. |
| 2006/0015089 A1 | 1/2006 | Meglin et al. |
| 2006/0052879 A1 | 3/2006 | Kolb |
| 2006/0074388 A1 | 4/2006 | Dextradeur et al. |
| 2006/0074409 A1 | 4/2006 | Schuermann |
| 2006/0146096 A1 * | 7/2006 | Wright ............... F15B 7/00 |
| | | 347/68 |
| 2006/0229553 A1 | 10/2006 | Hammack et al. |
| 2006/0229573 A1 | 10/2006 | Lamborne |
| 2006/0259151 A1 | 11/2006 | Ward |
| 2006/0271019 A1 | 11/2006 | Stoller et al. |
| 2007/0010797 A1 | 1/2007 | Nishtala et al. |
| 2007/0010798 A1 | 1/2007 | Stoller et al. |
| 2007/0055198 A1 | 3/2007 | O'Mahony et al. |
| 2007/0073271 A1 | 3/2007 | Brucker et al. |
| 2007/0088333 A1 | 4/2007 | Levin et al. |
| 2007/0112302 A1 | 5/2007 | Yu |
| 2007/0197957 A1 | 8/2007 | Hunter et al. |
| 2007/0208291 A1 | 9/2007 | Patel |
| 2007/0213665 A1 | 9/2007 | Curtin et al. |
| 2007/0219488 A1 | 9/2007 | Francescatti |
| 2007/0255230 A1 | 11/2007 | Gross et al. |
| 2008/0051678 A1 | 2/2008 | Lindahl |
| 2008/0051691 A1 | 2/2008 | Dragoon et al. |
| 2008/0058650 A1 | 3/2008 | Saadat et al. |
| 2008/0097463 A1 | 4/2008 | House |
| 2008/0119907 A1 | 5/2008 | Stahmann |
| 2008/0142023 A1 | 6/2008 | Schmid et al. |
| 2008/0183299 A1 | 7/2008 | Monga et al. |
| 2008/0215247 A1 | 9/2008 | Tonelli et al. |
| 2008/0243091 A1 | 10/2008 | Humphreys et al. |
| 2008/0255550 A1 | 10/2008 | Bell |
| 2008/0281291 A1 | 11/2008 | Tihon et al. |
| 2008/0288082 A1 | 11/2008 | Deal |
| 2008/0312550 A1 | 12/2008 | Nishtala et al. |
| 2009/0024091 A1 | 1/2009 | Li et al. |
| 2009/0030370 A1 | 1/2009 | Nishtala et al. |
| 2009/0030435 A1 | 1/2009 | Burnett et al. |
| 2009/0043229 A1 | 2/2009 | Dunn et al. |
| 2009/0088677 A1 | 4/2009 | Cohen |
| 2009/0093748 A1 | 4/2009 | Patterson et al. |
| 2009/0105719 A1 | 4/2009 | Honey et al. |
| 2009/0143713 A1 | 6/2009 | Van Dam et al. |
| 2009/0162530 A1 | 6/2009 | Nesbitt |
| 2009/0171137 A1 | 7/2009 | Farnan et al. |
| 2009/0171241 A1 | 7/2009 | Garcia et al. |
| 2009/0281507 A1 | 11/2009 | Humphreys |
| 2009/0318844 A1 | 12/2009 | Burnett |
| 2010/0057000 A1 | 3/2010 | Melsheimer et al. |
| 2010/0081148 A1 | 4/2010 | Singbartl et al. |
| 2010/0086580 A1 | 4/2010 | Nyman et al. |
| 2010/0121159 A1 | 5/2010 | Burnett et al. |
| 2010/0191183 A1 | 7/2010 | Tanghoej et al. |
| 2010/0204682 A1 | 8/2010 | Tanghoj et al. |
| 2010/0241240 A1 | 9/2010 | Willard et al. |
| 2010/0261985 A1 | 10/2010 | Cohen-Solal et al. |
| 2010/0298857 A1 | 11/2010 | Zook et al. |
| 2010/0312163 A1 | 12/2010 | Forsell |
| 2011/0009799 A1 | 1/2011 | Mullick et al. |
| 2011/0009831 A1 | 1/2011 | Burkholz et al. |
| 2011/0015558 A1 | 1/2011 | Kaye et al. |
| 2011/0077605 A1 | 3/2011 | Karpowicz et al. |
| 2011/0089111 A1 | 4/2011 | Mori et al. |
| 2011/0098683 A1 | 4/2011 | Wiita et al. |
| 2011/0118537 A1 | 5/2011 | Wampler |
| 2011/0132838 A1 | 6/2011 | Curtis et al. |
| 2011/0208319 A1 | 8/2011 | Laster |
| 2011/0230950 A1 | 9/2011 | Knapp |
| 2011/0238163 A1 | 9/2011 | Andrews et al. |
| 2011/0269167 A1 | 11/2011 | Bene |
| 2011/0276024 A1 | 11/2011 | Randolph et al. |
| 2011/0282264 A1 | 11/2011 | Hurt |
| 2011/0301553 A1 | 12/2011 | Goral et al. |
| 2011/0301662 A1 | 12/2011 | Bar-Yoseph et al. |

(56) References Cited

U.S. PATENT DOCUMENTS

| | | |
|---|---|---|
| 2012/0029937 A1 | 2/2012 | Neftel et al. |
| 2012/0042427 A1 | 2/2012 | Messier |
| 2012/0053700 A1 | 3/2012 | Rickner |
| 2012/0078226 A1 | 3/2012 | Latere Dwan'isa et al. |
| 2012/0083899 A1 | 4/2012 | Whitmore, III |
| 2012/0107420 A1 | 5/2012 | Breit et al. |
| 2012/0136343 A1 | 5/2012 | Burnett |
| 2012/0154264 A1 | 6/2012 | Wang et al. |
| 2012/0165641 A1 | 6/2012 | Burnett et al. |
| 2012/0179144 A1 | 7/2012 | Carleo |
| 2012/0179145 A1 | 7/2012 | Nishtala et al. |
| 2012/0220926 A1 | 8/2012 | Soykan et al. |
| 2012/0238802 A1 | 9/2012 | Knight et al. |
| 2012/0265020 A1 | 10/2012 | Pandey et al. |
| 2012/0277155 A1 | 11/2012 | VanAntwerp et al. |
| 2012/0316656 A1 | 12/2012 | Deal et al. |
| 2013/0030262 A1 | 1/2013 | Burnett et al. |
| 2013/0066166 A1 | 3/2013 | Burnett et al. |
| 2013/0085468 A1 | 4/2013 | Buydenok |
| 2013/0090648 A1 | 4/2013 | Nagale et al. |
| 2013/0131621 A1 | 5/2013 | Van Holten et al. |
| 2013/0138077 A1 | 5/2013 | O'Day |
| 2013/0150828 A1 | 6/2013 | Conway |
| 2013/0172807 A1 | 7/2013 | Cruz |
| 2013/0172881 A1 | 7/2013 | Hill et al. |
| 2013/0184545 A1 | 7/2013 | Bloomqvist et al. |
| 2013/0187563 A1 | 7/2013 | Sasai et al. |
| 2013/0197471 A1 | 8/2013 | Williams et al. |
| 2013/0199998 A1 | 8/2013 | Kelly et al. |
| 2013/0218135 A1 | 8/2013 | Dein |
| 2013/0231640 A1 | 9/2013 | Terry et al. |
| 2013/0231752 A1 | 9/2013 | Rosenbaum et al. |
| 2013/0253409 A1 | 9/2013 | Burnett |
| 2013/0267845 A1 | 10/2013 | Howle et al. |
| 2013/0274644 A1 | 10/2013 | Hertz |
| 2013/0274783 A1 | 10/2013 | Wynberg |
| 2013/0303865 A1 | 11/2013 | Rebec et al. |
| 2013/0303961 A1 | 11/2013 | Wolff et al. |
| 2013/0304082 A1 | 11/2013 | Aklog et al. |
| 2013/0317322 A1 | 11/2013 | Andrijauskas |
| 2013/0331824 A1 | 12/2013 | Kim |
| 2013/0338580 A1* | 12/2013 | Yamatani .......... A61M 25/0041 604/525 |
| 2013/0345670 A1 | 12/2013 | Rajagopalan et al. |
| 2014/0031773 A1 | 1/2014 | Mikkaichi |
| 2014/0031787 A1 | 1/2014 | Burnes et al. |
| 2014/0039375 A1 | 2/2014 | Jimenez et al. |
| 2014/0058316 A1 | 2/2014 | Gupta et al. |
| 2014/0073926 A1 | 3/2014 | Rajendran et al. |
| 2014/0074144 A1 | 3/2014 | Shrivastava et al. |
| 2014/0135941 A1 | 5/2014 | Smouse et al. |
| 2014/0142539 A1 | 5/2014 | Salinas et al. |
| 2014/0148648 A1 | 5/2014 | Tycast et al. |
| 2014/0148754 A1 | 5/2014 | Soykan et al. |
| 2014/0155818 A1 | 6/2014 | Salinas et al. |
| 2014/0188248 A1 | 7/2014 | Gandhi |
| 2014/0188249 A1 | 7/2014 | Pendleton et al. |
| 2014/0214009 A1 | 7/2014 | Reyes |
| 2014/0228801 A1 | 8/2014 | Keeling |
| 2014/0275984 A1 | 9/2014 | Hermann et al. |
| 2014/0276341 A1 | 9/2014 | Ludin et al. |
| 2014/0276628 A1 | 9/2014 | Gandras et al. |
| 2014/0343515 A1 | 11/2014 | Sylvester et al. |
| 2014/0364820 A1 | 12/2014 | Solazzo et al. |
| 2015/0011855 A1* | 1/2015 | Burnett .............. A61M 5/14276 600/365 |
| 2015/0011928 A1 | 1/2015 | Burnett |
| 2015/0017682 A1 | 1/2015 | Adam |
| 2015/0065783 A1 | 3/2015 | Buelna |
| 2015/0080844 A1 | 3/2015 | Donavan et al. |
| 2015/0094548 A1 | 4/2015 | Sabatini et al. |
| 2015/0094644 A1 | 4/2015 | Lenihan et al. |
| 2015/0094696 A1 | 4/2015 | Adams, Jr. et al. |
| 2015/0100009 A1 | 4/2015 | Bearss |
| 2015/0134073 A1 | 5/2015 | Tang et al. |
| 2015/0164370 A1 | 6/2015 | Wabel et al. |
| 2015/0194052 A1 | 7/2015 | Sagan et al. |
| 2015/0223953 A1 | 8/2015 | Pendleton et al. |
| 2015/0224241 A1 | 8/2015 | Fontanazzi et al. |
| 2015/0273120 A1 | 10/2015 | Zamarripa et al. |
| 2015/0283362 A1 | 10/2015 | Shelton et al. |
| 2015/0290411 A1 | 10/2015 | Warrington et al. |
| 2015/0306364 A1 | 10/2015 | Shevgoor |
| 2015/0328027 A1 | 11/2015 | Nishio et al. |
| 2015/0352339 A1 | 12/2015 | Wang |
| 2016/0045302 A1 | 2/2016 | Nishio et al. |
| 2016/0051176 A1 | 2/2016 | Ramos et al. |
| 2016/0058489 A1 | 3/2016 | Fischell et al. |
| 2016/0183819 A1 | 6/2016 | Burnett et al. |
| 2016/0303303 A1 | 10/2016 | Rovatti et al. |
| 2016/0310711 A1 | 10/2016 | Luxon et al. |
| 2016/0331294 A1 | 11/2016 | Imran et al. |
| 2016/0367747 A1 | 12/2016 | Loske |
| 2017/0020724 A1 | 1/2017 | Burnett et al. |
| 2017/0021128 A1* | 1/2017 | Erbey, II .................. A61M 1/84 |
| 2017/0095323 A1 | 4/2017 | Garcia |
| 2017/0095641 A1 | 4/2017 | Scarpine et al. |
| 2017/0113000 A1 | 4/2017 | Tobescu et al. |
| 2017/0119519 A1 | 5/2017 | Sambusseti et al. |
| 2017/0128639 A1 | 5/2017 | Erbey, II et al. |
| 2017/0128654 A1* | 5/2017 | Feld ..................... A61M 25/10 |
| 2017/0136222 A1 | 5/2017 | Hakim et al. |
| 2017/0196576 A1 | 7/2017 | Long et al. |
| 2017/0197028 A1 | 7/2017 | Goldsmith |
| 2017/0232153 A1 | 8/2017 | Babu et al. |
| 2017/0266414 A1 | 9/2017 | Rocha-Singh et al. |
| 2017/0325927 A1 | 11/2017 | Gobel |
| 2017/0348507 A1 | 12/2017 | Erbey, II et al. |
| 2017/0348512 A1 | 12/2017 | Orr et al. |
| 2017/0367636 A1 | 12/2017 | Mantinband et al. |
| 2018/0001055 A1 | 1/2018 | Utas et al. |
| 2018/0116751 A1 | 5/2018 | Schwartz et al. |
| 2018/0117288 A1 | 5/2018 | Lindsay et al. |
| 2018/0147330 A1 | 5/2018 | Peng et al. |
| 2018/0169313 A1 | 6/2018 | Schwammenthal et al. |
| 2018/0177458 A1 | 6/2018 | Burnett |
| 2018/0193618 A1 | 7/2018 | Erbey, II et al. |
| 2018/0207412 A1 | 7/2018 | Malek et al. |
| 2018/0344250 A1 | 12/2018 | McKinney et al. |
| 2019/0030303 A1 | 1/2019 | Holman et al. |
| 2019/0091442 A1 | 3/2019 | Erbey, II et al. |
| 2019/0105465 A1 | 4/2019 | Erbey, II et al. |
| 2019/0201662 A1 | 7/2019 | Lad et al. |
| 2019/0240448 A1 | 8/2019 | Murdock |
| 2019/0247615 A1 | 8/2019 | Bishawi |
| 2020/0001045 A1 | 1/2020 | McIntyre |
| 2020/0094017 A1 | 3/2020 | Erbey, II et al. |
| 2021/0178133 A1 | 6/2021 | Walish et al. |

FOREIGN PATENT DOCUMENTS

| | | |
|---|---|---|
| CA | 2205473 C | 6/2006 |
| CN | 2175619 | 8/1994 |
| CN | 2562776 Y | 7/2003 |
| CN | 2588940 Y | 12/2003 |
| CN | 1479596 A | 3/2004 |
| CN | 2753382 Y | 1/2006 |
| CN | 2928043 Y | 8/2007 |
| CN | 101224148 A | 7/2008 |
| CN | 101426540 | 5/2009 |
| CN | 201814968 U | 5/2011 |
| CN | 102176928 A | 9/2011 |
| CN | 202459720 U | 10/2012 |
| CN | 202526754 U | 11/2012 |
| CN | 202802478 U | 3/2013 |
| CN | 103096964 A | 5/2013 |
| CN | 103203062 A | 7/2013 |
| CN | 103841905 A | 6/2014 |
| CN | 203777060 U | 8/2014 |
| CN | 203842151 U | 9/2014 |
| CN | 204158867 U | 2/2015 |
| CN | 204246651 U | 4/2015 |
| CN | 204446944 U | 7/2015 |
| CN | 205126495 U | 4/2016 |

(56) References Cited

FOREIGN PATENT DOCUMENTS

| | | |
|---|---|---|
| CN | 106237417 A | 12/2016 |
| CN | 106473847 A | 3/2017 |
| CN | 106693092 A | 5/2017 |
| CN | 107261294 A | 10/2017 |
| DE | 102012016049 A1 | 2/2014 |
| EP | 0873760 A1 | 10/1998 |
| EP | 1001803 B1 | 9/2004 |
| EP | 1980292 A2 | 10/2008 |
| EP | 3488897 A1 | 5/2019 |
| EP | 3970775 A1 | 3/2022 |
| FR | 3052671 A1 | 12/2017 |
| JP | 59111748 A | 6/1984 |
| JP | H42361 A | 1/1992 |
| JP | H10504469 | 5/1998 |
| JP | 2002510536 A | 4/2002 |
| JP | 2002291879 A | 10/2002 |
| JP | 200253888 | 11/2002 |
| JP | 2002537893 A | 11/2002 |
| JP | 2003530165 A | 10/2003 |
| JP | 2004215787 A | 8/2004 |
| JP | 2006516214 A | 6/2006 |
| JP | 2006526464 A | 11/2006 |
| JP | 2009505802 A | 2/2009 |
| JP | 2009238520 A | 10/2009 |
| JP | 2009537256 A | 10/2009 |
| JP | 201005282 A | 1/2010 |
| JP | 2010508984 A | 3/2010 |
| JP | 2010119737 A | 6/2010 |
| JP | 2010230618 | 10/2010 |
| JP | 2013149498 A | 1/2012 |
| JP | 2012505022 A | 3/2012 |
| JP | 2012530575 | 12/2012 |
| JP | 2014136116 A | 7/2014 |
| JP | 2014176689 A | 9/2014 |
| RU | 2113245 C1 | 6/1998 |
| RU | 2300399 C1 | 6/2007 |
| RU | 149161 U1 | 12/2014 |
| TW | M540625 U | 5/2017 |
| WO | 9529716 A1 | 11/1995 |
| WO | 9816171 A1 | 4/1998 |
| WO | 9850088 A1 | 11/1998 |
| WO | 0054701 A1 | 9/2000 |
| WO | 0160260 A1 | 8/2001 |
| WO | 03017870 A1 | 3/2003 |
| WO | 2006017439 A2 | 2/2006 |
| WO | 2006023589 A2 | 3/2006 |
| WO | 2006044621 A2 | 4/2006 |
| WO | 2007027830 A1 | 3/2007 |
| WO | 2008066625 A1 | 6/2008 |
| WO | 2010082197 A2 | 7/2010 |
| WO | 2011109570 A2 | 9/2011 |
| WO | 2011139498 A1 | 11/2011 |
| WO | 2013022005 A1 | 2/2013 |
| WO | 2013029622 A1 | 3/2013 |
| WO | 2014025367 A1 | 2/2014 |
| WO | 2014043650 A2 | 3/2014 |
| WO | 2014062225 A1 | 4/2014 |
| WO | 2015105916 A1 | 7/2015 |
| WO | 2015157467 A1 | 10/2015 |
| WO | 2015198333 A1 | 12/2015 |
| WO | 2016049654 A1 | 3/2016 |
| WO | 2016103256 A1 | 6/2016 |
| WO | 2017015345 A2 | 1/2017 |
| WO | 2017015351 A2 | 1/2017 |
| WO | 2017019974 A1 | 2/2017 |
| WO | 2017087182 A1 | 5/2017 |
| WO | 2018186781 A1 | 10/2018 |
| WO | 2018200050 A1 | 11/2018 |
| WO | 2019038730 A1 | 2/2019 |
| WO | 2020236748 A1 | 11/2020 |

OTHER PUBLICATIONS

U.S. Pat. No. 9,744,331 / U.S. Appl. No. 15/215,081, "Ureteral and Bladder Catheters and Methods of Inducing Negative Pressure to Increase Renal Perfusion", Aug. 29, 2017 / filed Jul. 20, 2016.
U.S. Pat. No. 10,512,713 / U.S. Appl. No. 15/411,884, "Method of Removing Excess Fluid from a Patient with Hemodilution", Dec. 24, 2019 / filed Jan. 20, 2017.
U.S. Appl. No. 15/673,706, "Ureteral and Bladder Catheters and Methods of Inducing Negative Pressure to Increase Renal Perfusion", filed Aug. 10, 2017.
U.S. Appl. No. 15/687,064, "Ureteral and Bladder Catheters and Methods of Inducing Negative Pressure to Increase Renal Perfusion", filed Aug. 25, 2017.
U.S. Appl. No. 15/687,083, "Ureteral and Bladder Catheters and Methods of Inducing Negative Pressure to Increase Renal Perfusion", filed Aug. 25, 2017.
U.S. Appl. No. 15/879,976, "Ureteral and Bladder Catheters and Methods of Inducing Negative Pressure to Increase Renal Perfusion", filed Jan. 25, 2018.
U.S. Appl. No. 15/879,869, "Catheter Device and Method for Inducing Negative Pressure in a Patient's Bladder", filed Jan. 25, 2018.
U.S. Appl. No. 15/745,823, "Catheter Device and Method for Inducing Negative Pressure in a Patient's Bladder", filed Jul. 20, 2016.
U.S. Appl. No. 15/879,770, "Systems, Kits and Methods for Inducing Negative Pressure to Increase Renal Function", filed Jan. 25, 2018.
U.S. Appl. No. 16/012,233, "Ureteral and Bladder Catheters and Methods of Inducing Negative Pressure to Increase Renal Perfusion", filed Jun. 19, 2018.
U.S. Appl. No. 16/036,971, "Ureteral and Bladder Catheters and Methods of Inducing Negative Pressure to Increase Renal Perfusion", filed Jul. 17, 2018.
U.S. Appl. No. 16/206,207, "Percutaneous Ureteral Catheter", filed Nov. 30, 2018.
U.S. Appl. No. 16/206,389, "Coated Ureteral Catheter or Ureteral Stent and Method", filed Nov. 30, 2018.
U.S. Pat. No. 10,493,232 / U.S. Appl. No. 16/205,987, "Ureteral Catheters, Bladder Catheters, Systems, Kits and Methods for Inducing Negative Pressure to Increase Renal Function", Dec. 3, 2019 / filed Nov. 30, 2018.
U.S. Pat. No. 10,426,919 / U.S. Appl. No. 16/257,791, "Systems and Methods for Inducing Negative Pressure in a Portion of a Urinary Tract of a Patient", Oct. 1, 2019 filed Jan. 25, 2019.
U.S. Appl. No. 16/390,154, "Ureteral and Bladder Catheters and Methods ofInducing Negative Pressure to Increase Renal Perfusion", filed Apr. 22, 2019.
U.S. Appl. No. 16/542,680, "Systems and Methods for Inducing NegativePressure in a Portion of a Urinary Tract of a Patient", filed Aug. 16, 2019.
U.S. Appl. No. 16/670,249, "Method of Removing Excess Fluids from aPatient with Hemodilution", filed Oct. 31, 2019.
U.S. Appl. No. 16/662,536, "Ureteral Catheters, Bladder Catheters, Systems, Kits and Methods for Inducing Negative Pressure to Increase Renal Function", filed Oct. 24, 2019.
U.S. Appl. No. 16/662,212, "Catheter and Method for Inducing Negative Pressure in a Patient's Bladder", filed Oct. 24, 2019.
U.S. Appl. No. 16/696,026, "Coated and/or Impregnated Ureteral Catheteror Stent and Method", filed Nov. 26, 2019.
Mordi et al., "Renal and Cardiovascular Effects of Sodium-glucose contransporter 2 (SGLT2) inhibition in combination with loop Diuretics in diabetic patients with Chronic Heart Failure (RECEDE-CHF): protocol for a randomised controlled double-blind cross-over trial", BMJ Open, 2017, pp. 1-9.
Quadra-Coil | Olympus America | Medical, Ureteral Stents, https://www.medical.olympusamerica.com/products/quadra-coil (downloaded from the Internet Aug. 31, 2022) 2 pages.
Stents—Urology | Olympus America | Medical. Ureteral Stents, https://www.medical.olympusamerica.com/products/stents-Urology (downloaded from the Internet Aug. 31, 2022) 2 pages.
Ureteral stent—Quadra-Coil—Olympus Medical Europa, https://www.medicalexpo.com/prod/olympus-medical-europa/product-69587-661607.html (downloaded from the Internet Aug. 31, 2022) 5 pages.

(56) References Cited

OTHER PUBLICATIONS

Johnson et al., "Clinical Practice Guidelines for Chronic Kidney Disease in Adults: Part I. Definition, Disease Stages, Evaluation, Treatment, and Risk Factors", American Family Physician, Sep. 1, 2004, p. 869-876, vol. 70 Issue 5.
Damman et al., "Increased Central Venous Pressure Is Associated With Impaired Renal Function and Mortality in a Broad Spectrum of XPatients With Cardiovascular Disease", 2009, Journal of the American College of Cardiology, vol. 53:7, pp. 582-588.
Dixon et al., "The musculature of the human renal calices, pelvis and upper ureter", J, Anat., 1982, vol. 135, pp. 129-137.
Gregersen et al., "Regional Differences Exist in Elastic Wall Properties in the Ureter", SJUN, 1996, vol. 30, pp. 343-348.
Kiil, "Urinary Flow and Ureteral Peristalsis" in: Lutzeyer W., Melchior H. (Eds.) Urodynamics, 1973 Springer, Berlin, Heidelberg (pp. 57-70).
Lala et al., "Relief and Recurrence of Congestion During and After Hospitalization for Acute Heart Failure: Insights from DOSE-AHF and CARRESS-HF", Circ Heart Fail, 2015, vol. 8:4, pp. 741-748.
Legrand et al. "Association between systemic hemodynamics and septic acute kidney injury in critically ill patients: a retrospective observational study", Critical Care, 2013, vol. 17:R278, pp. 1-8.
Nohria et al., "Cardiorenal Interactions Insights from the ESCAPE Trial", Heart Failure, 2008, vol. 51:13, pp. 1268-1274.
Uthoff et al., "Central venous pressure and impaired renal function in patients with acute heart failure", European Journal of Heart Failure, 2011. vol. 13, pp. 432-439.
Walker, "Annals of Surgery" 1913, Lippincott Williams & Wilkins, p. 58, Figures 3 and 9.
Webb, "Percutaneous Renal Surgery: A Practical Clinical Handbook", 2016, Springer International Publishing, Switzerland, p. 92.
Woodburne et al., "The Uretal Lumen during Peristalsis", Am. J. Anat., 1972. vol. 133, pp. 255-258.
Bart et al.; "Ultrafiltration in Decompensated Heart Failure with Cardiorenal Syndrome"; N Engl J Med; 2012; p. 2296-2304; vol. 367.
Burr et al.; "Urinary catheter blockage depends on urine pH, calcium and rate of flow"; Spinal Cord; 1997; pp. 521-525; vol. 35.
Clinical Practice Guidelines for Chronic Kidney Disease: Evaluation, Classification and Stratification; National Kidney Foundation; Am. J. Kidney Dis.; 2002; pp. S1-S266; Suppl. 1.
"The Criteria Committee of the New York Heart Association", (1994), Nomenclature and Criteria for Diagnosis of Diseases of the Heart and Great Vessels, (9th ed.), Boston: Little, Brown & Co. pp. 253-256 (Abstract).
Harris et al., "Relationship between patients' outcomes and the changes in serum creatinine and urine output and RIFLE classification in a large critical care cohort database", Kidney International, 2015, pp. 369-377, vol. 88.
Jessup et al.; "The Cardiorenal Syndrome—Do We Need a Change of Strategy or a Change of Tactics?"; Journal of the American College of Cardiology; 2009; pp. 597-599; vol. 53:7.
Mardis et al., "Comparative Evaluation of Materials Used for Internal Ureteral Stents", Journal of Endourology, 1993, p. 105-115, vol. 7, No. 2.
Mullens et al.; "Importance of Venous Congestion for Worsening of Renal Function in Advanced Decompensated Heart Failure"; Journal of the American College of Cardiology; 2009; pp. 589-596; vol. 53:7.
Peters et al.; "Short and Long-Term Effects of the Angiotensin II Receptor Blocker Irbesartan on Intradialytic Central Hemodynamics: A Randomized Double-Blind Placebo-Controlled One-Year Intervention Trial (the SAFIR Study)"; PLoS One; Jun. 1, 2015; pp. 1-22.
"Standard Specification for Ureteral Stents", ASTM International, 2014, Designation F1828-97, p. 1-6.
Verbrugge et al.; "The kidney in congestive heart failure: 'are natriuresis, sodium, and diuretics really the good, the bad and the ugly?'"; European Journal of Heart Failure; 2014; pp. 133-142; vol. 16.
Wolf, Jr. et al.; "Comparative Ureteral Microanatomy"; Journal of Endourology; 1996; pp. 527-531; vol. 10:6.
Zelenko et al.; "Normal Ureter Size on Unenhanced Helical CT"; American Journal of Roentgenology; 2004; pp. 1039-1041; vol. 182.

\* cited by examiner

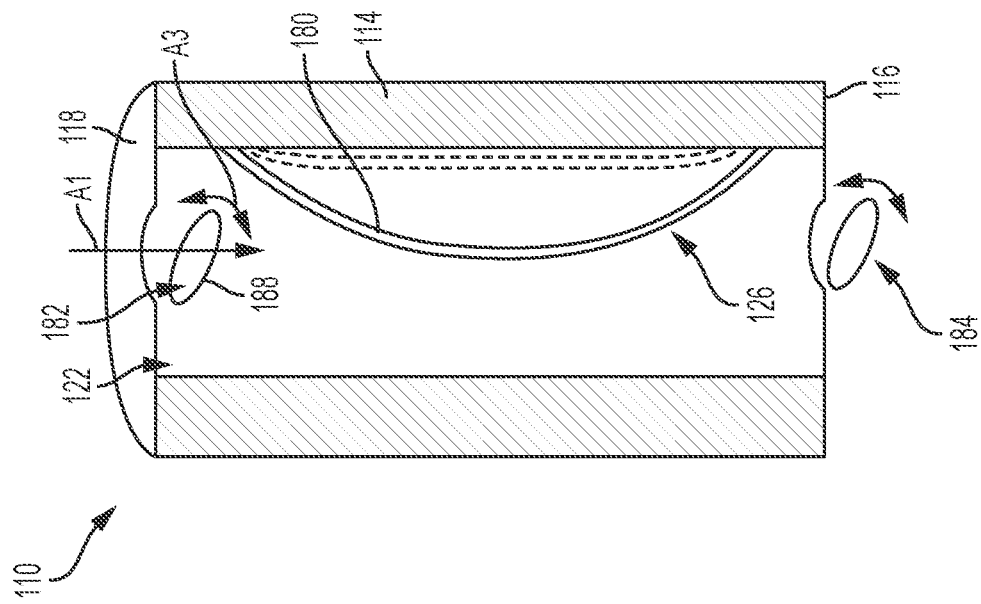
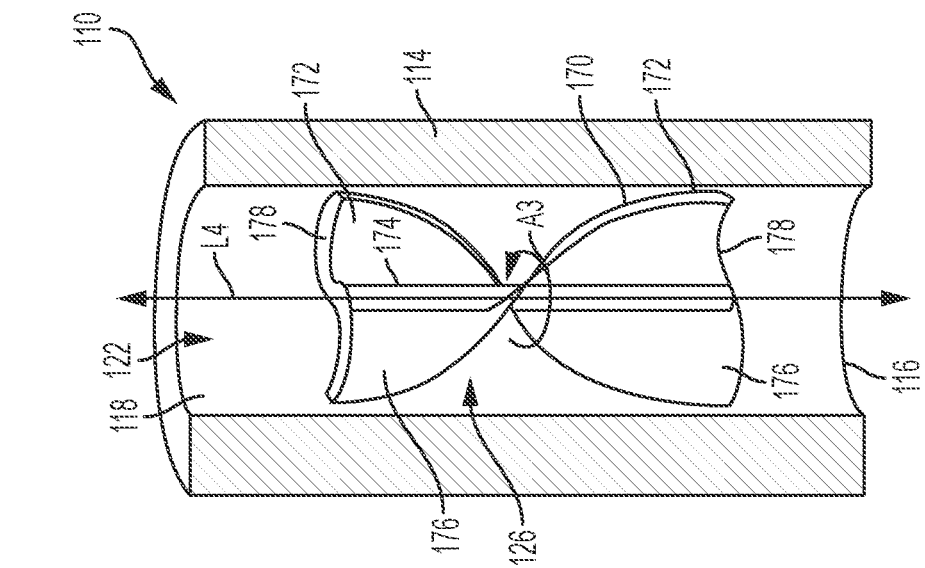
FIG. 8
FIG. 7

INDWELLING PUMP FOR FACILITATING REMOVAL OF URINE FROM THE URINARY TRACT

CROSS REFERENCE TO RELATED APPLICATIONS

This application is the United States national phase of International Application No. PCT/IB2018/056444 filed Aug. 24, 2018, and claims benefit of U.S. Provisional Patent Application No. 62/550,259, filed Aug. 25, 2017, which is incorporated herein by reference in its entirety.

BACKGROUND

Technical Field

The present disclosure relates to a pump for deployment within a body lumen and, for example, to a pump sized for insertion and deployment within a patient's urinary tract for inducing negative and/or positive pressure in a patient's bladder, ureter(s), and/or kidney(s).

Background

The renal or urinary system includes a pair of kidneys, each kidney being connected by a ureter to the bladder, and a urethra for draining urine produced by the kidneys from the bladder. The kidneys perform several vital functions for the human body including, for example, filtering the blood to eliminate waste in the form of urine. The kidneys also regulate electrolytes (e.g., sodium, potassium and calcium) and metabolites, blood volume, blood pressure, blood pH, fluid volume, production of red blood cells, and bone metabolism. Adequate understanding of the anatomy and physiology of the kidneys is useful for understanding the impact that altered hemodynamics and other fluid overload conditions have on their function.

In normal anatomy, the two kidneys are located retroperitoneally in the abdominal cavity. The kidneys are bean-shaped encapsulated organs. Urine is formed by nephrons, the functional unit of the kidney, and then flows through a system of converging tubules called collecting ducts. The collecting ducts join together to form minor calyces, then major calyces, which ultimately join near the concave portion of the kidney (renal pelvis). A major function of the renal pelvis is to direct urine flow to the ureter. Urine flows from the renal pelvis into the ureter, a tube-like structure that carries the urine from the kidneys into the bladder. The outer layer of the kidney is called the cortex and is a rigid fibrous encapsulation. The interior of the kidney is called the medulla. The medulla structures are arranged in pyramids.

Each kidney is made up of approximately one million nephrons. Each nephron includes the glomerulus, Bowman's capsule, and tubules. The tubules include the proximal convoluted tubule, the loop of Henle, the distal convoluted tubule, and the collecting duct. The nephrons contained in the cortex layer of the kidney are distinct from the anatomy of those contained in the medulla. The principal difference is the length of the loop of Henle. Medullary nephrons contain a longer loop of Henle, which, under normal circumstances, allows greater regulation of water and sodium reabsorption than in the cortex nephrons.

The glomerulus is the beginning of the nephron and is responsible for the initial filtration of blood. Afferent arterioles pass blood into the glomerular capillaries, where hydrostatic pressure pushes water and solutes into Bowman's capsule. Net filtration pressure is expressed as the hydrostatic pressure in the afferent arteriole minus the hydrostatic pressure in Bowman's space minus the osmotic pressure in the efferent arteriole.

Net Filtration Pressure=Hydrostatic Pressure (Afferent Arteriole)−Hydrostatic Pressure (Bowman's Space)−Osmotic Pressure (Efferent Arteriole)  (Equation 1)

The magnitude of this net filtration pressure defined by Equation 1 determines how much ultra-filtrate is formed in Bowman's space and delivered to the tubules. The remaining blood exits the glomerulus via the efferent arteriole. Normal glomerular filtration, or delivery of ultra-filtrate into the tubules, is about 90 ml/min/1.73 m$^2$.

The glomerulus has a three-layer filtration structure, which includes the vascular endothelium, a glomerular basement membrane, and podocytes. Normally, large proteins such as albumin and red blood cells, are not filtered into Bowman's space. However, elevated glomerular pressures and mesangial expansion create surface area changes on the basement membrane and larger fenestrations between the podocytes allowing larger proteins to pass into Bowman's space.

Ultra-filtrate collected in Bowman's space is delivered first to the proximal convoluted tubule. Reabsorption and secretion of water and solutes in the tubules is performed by a mix of active transport channels and passive pressure gradients. The proximal convoluted tubules normally reabsorb a majority of the sodium chloride and water and nearly all glucose and amino acids that were filtered by the glomerulus. The loop of Henle has two components that are designed to concentrate wastes in the urine. The descending limb is highly water permeable and reabsorbs most of the remaining water. The ascending limb reabsorbs 25% of the remaining sodium chloride, creating a concentrated urine, for example, in terms of urea and creatinine. The distal convoluted tubule normally reabsorbs a small proportion of sodium chloride, and the osmotic gradient creates conditions for the water to follow.

Under normal conditions, there is a net filtration of approximately 14 mmHg. The impact of venous congestion can be a significant decrease in net filtration, down to approximately 4 mmHg. See Jessup M., *The cardiorenal syndrome: Do we need a change of strategy or a change of tactics?*, JACC 53(7):597-600, 2009 (hereinafter "Jessup"). The second filtration stage occurs at the proximal tubules. Most of the secretion and absorption from urine occurs in tubules in the medullary nephrons. Active transport of sodium from the tubule into the interstitial space initiates this process. However, the hydrostatic forces dominate the net exchange of solutes and water. Under normal circumstances, it is believed that 75% of the sodium is reabsorbed back into lymphatic or venous circulation. However, because the kidney is encapsulated, it is sensitive to changes in hydrostatic pressures from both venous and lymphatic congestion. During venous congestion, the retention of sodium and water can exceed 85%, further perpetuating the renal congestion. See Verbrugge et al., *The kidney in congestive heart failure: Are natriuresis, sodium, and diuretics really the good, the bad and the ugly?* European Journal of Heart Failure 2014:16, 133-42 (hereinafter "Verbrugge"). Venous congestion may result from, for example, heart failure, sepsis, burns, and other primary morbidities affecting renal pressure gradients and nephron filtration.

Venous congestion can lead to a prerenal form of acute kidney injury (AKI). Prerenal AKI is due to a loss of perfusion (or loss of blood flow) through the kidney. Many clinicians focus on the lack of flow into the kidney due to shock. However, there is also evidence that a lack of blood flow out of the organ due to venous congestion can be a clinically important sustaining injury. See Damman, K., *Importance of venous congestion for worsening renal function in advanced decompensated heart failure*, JACC 17:589-96, 2009 (hereinafter "Damman").

Prerenal AKI occurs across a wide variety of diagnoses requiring critical care admissions. The most prominent admissions are for sepsis and Acute Decompensated Heart Failure (ADHF). Additional admissions include cardiovascular surgery, general surgery, cirrhosis, trauma, burns, and pancreatitis. While there is wide clinical variability in the presentation of these disease states, a common denominator is an elevated central venous pressure. In the case of ADHF, the elevated central venous pressure caused by heart failure leads to pulmonary edema, and, subsequently, to dyspnea, which necessitates the admission. In the case of sepsis, the elevated central venous pressure is largely a result of aggressive fluid resuscitation. Whether the primary insult was low perfusion due to hypovolemia or sodium and fluid retention, the sustaining injury is the venous congestion resulting in inadequate perfusion.

Hypertension is another widely recognized state that creates perturbations within the active and passive transport systems of the kidney(s). Hypertension directly impacts afferent arteriole pressure and results in a proportional increase in net filtration pressure within the glomerulus. The increased filtration fraction also elevates the peritubular capillary pressure, which stimulates sodium and water reabsorption. See Verbrugge.

Because the kidney is an encapsulated organ, it is sensitive to pressure changes in the medullary pyramids. The elevated renal venous pressure creates congestion that leads to a rise in the interstitial pressures. The elevated interstitial pressures exert forces upon both the glomerulus and tubules. See Verburgge. In the glomerulus, the elevated interstitial pressures directly oppose filtration. The increased pressures increase the interstitial fluid, thereby increasing the hydrostatic pressures in the interstitial fluid and peritubular capillaries in the medulla of the kidney. In both instances, hypoxia can ensue leading to cellular injury and further loss of perfusion. The net result is a further exacerbation of the sodium and water reabsorption creating a negative feedback. See Verbrugge, 133-42. Fluid overload, particularly in the abdominal cavity, is associated with many diseases and conditions, including elevated intra-abdominal pressure, abdominal compartment syndrome, and acute renal failure. Fluid overload can be addressed through renal replacement therapy. See Peters, C. D., *Short and Long-Term Effects of the Angiotensin II Receptor Blocker Irbesartanon Intradialytic Central Hemodynamics: A Randomized Double-Blind Placebo-Controlled One-Year Intervention Trial* (*the SAFIR Study*), *PLoS ONE* (2015) 10(6): e0126882. doi:10.1371/journal.pone.0126882 (hereinafter "Peters"). However, such a clinical strategy provides no improvement in renal function for patients with the cardiorenal syndrome. See Bart, B., *Ultrafiltration in decompensated heart failure with cardiorenal syndrome, NEJM* 2012; 367:2296-2304 (hereinafter "Bart").

In view of such problematic effects of fluid retention, devices and methods for improving removal of urine from the urinary tract and, for example, for increasing quantity and quality of urine output from the kidneys, are needed.

SUMMARY

In some examples, a pump assembly is provided comprising: (a) a pump module, wherein at least a portion of the pump module is configured to be positioned within at least one of an interior portion of a ureter, an interior portion of a renal pelvis, an interior portion of a bladder, or an interior portion of a urethra of a patient for providing negative pressure to at least one of the patient's ureter or kidney, the pump module comprising: a housing comprising an open proximal end, an open distal end, and a sidewall extending therebetween defining a flow channel for conducting fluid through at least one of the interior portion of the patient's ureter, the interior portion of the patient's renal pelvis, the interior portion of the patient's bladder, or the interior portion of the patient's urethra wherein at least a portion of the housing is configured to be positioned within at least one of the interior portion of the ureter, the interior portion of the renal pelvis, the interior portion of the bladder, or the interior portion of a urethra of a patient; and a pump element at least partially positioned within the channel configured to draw fluid through the channel between the open distal end and the open proximal end of the housing; and (b) a control module coupled to the pump module, the control module being configured to direct motion of the pump element to control flow rate of fluid passing through the channel, the control module comprising a housing configured to be positioned within at least one of a second interior portion of the patient's ureter, a second interior portion of the patient's renal pelvis, a second interior portion of the patient's bladder, or a second interior portion of the patient's urethra.

In some examples, a pump assembly is provided for inducement of negative pressure in a bladder of a patient, the assembly comprising: a pump module, wherein at least a portion of the pump module is configured to be positioned in a portion of a bladder of a patient, the pump module comprising a housing comprising an open proximal end, an open distal end, and a sidewall extending therebetween, the housing defining a flow channel for conducting fluid through an interior portion of a patient's bladder, and a pump element at least partially positioned within the channel that that is configured to draw fluid through the channel between the open distal end and the open proximal end of the housing; a bladder wall support for maintaining at least a portion of the bladder wall in an un-collapsed state in which ureter orifices are not occluded by the bladder wall; and a drainage catheter extending from the proximal end of the pump module through the urethra and from the patient's body, the drainage catheter comprising a drainage channel in fluid communication with the channel of the pump module for directing fluid expelled from the pump module from the body.

In some examples, a pump assembly is provided comprising: (a) a pump module, wherein at least a portion of the pump module is configured to be positioned within at least one of an interior portion of a ureter, an interior portion of a renal pelvis, an interior portion of a bladder, or an interior portion of a urethra of a patient for providing negative pressure to at least one of the patient's ureter or kidney, the pump module comprising: a housing comprising an open proximal end, an open distal end, and a sidewall extending therebetween defining a flow channel for conducting fluid through at least one of the interior portion of the patient's ureter, the interior portion of the patient's renal pelvis, or the interior portion of the patient's bladder, wherein at least a portion of the housing comprises a drainage channel comprising a distal portion configured to be positioned within at least one of a distal interior portion of the ureter or the interior portion of the renal pelvis of a patient; a pump element at least partially positioned within the channel configured to draw fluid through the channel between the open distal end and the open proximal end of the housing; and (b) a control module coupled to the pump module, the control module being configured to direct motion of the pump element to control flow rate of fluid passing through the channel, the control module comprising a housing configured to be positioned within a second interior portion of the patient's ureter, a second portion of the patient's renal pelvis, a second interior portion of the patient's bladder, or a second interior portion of the patient's urethra wherein the drainage channel is formed integrally with the housing or as a separate tube or conduit in fluid connection with the open distal end of the housing.

In some examples, a system is provided for providing negative pressure therapy to a patient's ureter and/or kidney, the system comprising: a pump assembly, comprising: (a) a pump module, wherein at least a portion of the pump module is configured to be positioned within at least one of an interior portion of a ureter, an interior portion of a renal pelvis, an interior portion of a bladder, or an interior portion of a urethra of a patient for providing negative pressure to at least one of the patient's ureter or kidney, the pump module comprising: a housing comprising an open proximal end, an open distal end, and a sidewall extending therebetween defining a flow channel for conducting fluid through at least one of the interior portion of the patient's ureter, the interior portion of the patient's renal pelvis, the interior portion of the patient's bladder or the internal portion of the patient's urethra, wherein at least a portion of the housing is configured to be positioned within at least one of the interior portion of the ureter, the interior portion of the renal pelvis the interior portion of the bladder, or the interior portion of the urethra of the patient; and a pump element at least partially positioned within the channel configured to draw fluid through the channel between the open distal end and the open proximal end of the housing; and (b) a control module coupled to the pump module, the control module being configured to direct motion of the pump element to control flow rate of fluid passing through the channel, the control module comprising a housing configured to be positioned in at least one of a second interior portion of the patient's ureter, a second interior portion of the patient's renal pelvis, a second interior portion of the patient's bladder, or a second interior portion of the patient's urethra; a power supply for providing power to the pump assembly; and a remote control device in wired or wireless communication with the control module, the remote control device being configured to provide instructions to the control module for operating the pump assembly and to receive information from the control module about at least one of the pump module or the patient.

In some examples, a method is provided for treating a patient by providing negative pressure therapy to a portion of the patient's urinary tract, the method comprising: positioning a pump assembly comprising: (a) a pump module, wherein at least a portion of the pump module is configured to be positioned within at least one of an interior portion of a ureter, an interior portion of a renal pelvis, an interior portion of a bladder, or an interior portion of a urethra of a patient for providing negative pressure to at least one of the patient's ureter or kidney, the pump module comprising: a housing comprising an open proximal end, an open distal end, and a sidewall extending therebetween defining a flow channel for conducting fluid through at least one of the interior portion of the patient's ureter, the interior portion of the patient's renal pelvis, or the interior portion of the patient's bladder, wherein at least a portion of the housing is configured to be positioned within at least one of the interior portion of the ureter, the interior portion of the renal pelvis, the interior portion of the bladder, or the interior portion of the urethra of the patient; and a pump element at least partially positioned within the channel configured to draw fluid through the channel between the open distal end and the open proximal end of the housing; and (b) a control module coupled to the pump module, the control module being configured to direct motion of the pump element to control flow rate of fluid passing through the channel, the control module comprising a housing configured to be positioned within at least one of a second interior portion of the patient's ureter, a second interior portion of the patient's renal pelvis, a second interior portion of the patient's bladder, or a second interior portion of the patient's urethra; and activating the pump module thereby causing the pump module to draw fluid through the channel thereof to deliver negative pressure to a portion of the patient's urinary tract.

Non-limiting examples of the present invention will now be described in the following numbered clauses:

Clause 1: A pump assembly comprising: (a) a pump module, wherein at least a portion of the pump module is configured to be positioned within at least one of an interior portion of a ureter, an interior portion of a renal pelvis, an interior portion of a bladder, or an interior portion of a urethra of a patient for providing negative pressure to at least one of the patient's ureter or kidney, the pump module comprising: a housing comprising an open proximal end, an open distal end, and a sidewall extending therebetween defining a flow channel for conducting fluid through at least one of the interior portion of the patient's ureter, the interior portion of the patient's renal pelvis, the interior portion of the patient's bladder or the interior portion of the patient's urethra, wherein at least a portion of the housing is configured to be positioned within at least one of the interior portion of the ureter, the interior portion of the renal pelvis, the interior portion of the bladder, or the interior portion of the urethra of a patient; and a pump element at least partially positioned within the channel configured to draw fluid through the channel between the open distal end and the open proximal end of the housing; and (b) a control module coupled to the pump module, the control module being configured to direct motion of the pump element to control flow rate of fluid passing through the channel, the control module comprising a housing configured to be positioned within at least one of a second interior portion of the patient's ureter, a second interior portion of the patient's renal pelvis, a second interior portion of the patient's bladder, or a second interior portion of the patient's urethra.

Clause 2: The pump assembly of claim 1, wherein a maximum outer diameter of the pump module housing is less than a maximum outer diameter of the control module housing.

Clause 3: The pump assembly of claim 2, wherein the maximum outer diameter of the pump module housing is about 0.5 mm to about 5.0 mm.

Clause 4: The pump assembly of any one of the preceding claims, wherein a maximum outer diameter of the control module housing is larger than an interior diameter of the patient's ureter, such that the control module does not pass from the patient's bladder into the ureter.

Clause 5: The pump assembly of any one of the preceding claims, wherein the pump module housing comprises one or more retention members extending from the sidewall for releasably attaching a portion of the pump module housing to at least one of the interior portion of the ureter, the interior portion of the renal pelvis, or an interior portion of the bladder of a patient.

Clause 6: The pump assembly of claim 5, wherein the retention members are retractable to permit removal of the pump module from the ureter, renal pelvis or the bladder.

Clause 7: The pump assembly of claim 5, wherein the retention members have a length when extended of less than about 3 mm.

Clause 8: The pump assembly of any one of the preceding claims, wherein the control module housing comprises one or more retention members extending therefrom for releasably attaching the control module housing to an interior portion of the bladder of a patient.

Clause 9: The pump assembly of any one of the preceding claims, wherein at least a portion of the housing comprises a drainage channel comprising a distal portion configured to be positioned within at least one of a distal interior portion of the ureter and/or the interior portion of the renal pelvis of a patient.

Clause 10: The pump assembly of claim 9, wherein the drainage channel is formed integrally with the housing or as a separate tube or conduit in fluid connection with the open distal end of the housing.

Clause 11: The pump assembly of claim 9 or 10, wherein the distal portion of the drainage channel comprises a coil.

Clause 12: The pump assembly of claims 9, 10 or 11, wherein the coil comprises one or more perforations in a sidewall of the coil.

Clause 13: The pump assembly of claims 9, 10, 11 or 12, wherein the coil comprises one or more perforations in an inwardly facing side of a sidewall of the coil.

Clause 14: The pump assembly of any one of the preceding claims, wherein the pump module housing is integrally formed with or connected to the control module housing.

Clause 15: The pump assembly of any one of the preceding claims, wherein the control module housing is a generally cylindrical housing comprising an open distal end connected to the open proximal end of the pump module housing, an open proximal end, and a flow channel in fluid communication with the flow channel of the pump module housing and extending between the proximal end and the distal end of the control module housing.

Clause 16: The pump assembly of any one of the preceding claims, wherein the control module housing is separate from the pump module housing and wherein electronic circuitry of the control module is operatively connected to the pump module via a wired or wireless connection.

Clause 17: The pump assembly of any one of the preceding claims, wherein the pump element comprises an impeller positioned within the channel of the pump module housing which rotates to draw fluid through the channel.

Clause 18: The pump assembly of any one of the preceding claims, wherein the pump element comprises a piezoelectric diaphragm positioned within the channel that can be configured to alternately extend from and retract to an inner surface of the sidewall to draw fluid through the channel.

Clause 19: The pump assembly of claim 18, wherein the pump module further comprises a distal valve positioned in a portion of the channel distal to the pump element and a proximal valve positioned in a portion of the channel proximal to the pump element.

Clause 20: The pump assembly of claim 19, wherein the distal valve and the proximal valve each comprise a one-way check valve configured to produce one-directional flow of fluid through the channel from the distal end to the proximal end thereof.

Clause 21: The pump assembly of any one of the preceding claims, wherein the pump module is configured to provide negative pressure of between about 0 mmHg and about 150 mmHg.

Clause 22: The pump assembly of any one of the preceding claims, wherein the pump module is configured to produce a negative pressure in the ureter sufficient for establishing a pressure gradient across filtration anatomy of a kidney of a patient to facilitate urine flow towards the ureter.

Clause 23: The pump assembly of any one of the preceding claims, further comprising a battery positioned in at least one of the control module housing or the pump module housing for providing power to at least one of the control module or pump element.

Clause 24: The pump assembly of claim 23, wherein the battery is rechargeable.

Clause 25: The pump assembly of any one of the preceding claims, wherein the control module comprises a wireless transceiver configured to receive operating instructions from a remote device and to provide information about negative pressure treatment from the control module to the remote device.

Clause 26: The pump assembly of any one of the preceding claims, further comprising an induction coil electronically coupled to at least one of the pump module or the control module for providing power thereto, the induction coil being configured to generate power when exposed to an electromagnetic field generated by a remote device positioned outside or within the patient's body.

Clause 27: The pump assembly of claim 26, wherein the induction coil comprises a conductive wire at least partially disposed on a flexible substrate.

Clause 28: The pump assembly of claim 27, wherein the flexible substrate is transitionable from a rolled configuration in which the flexible substrate is rolled about a central axis thereof to a size suitable for delivery through a catheter to a deployed configuration in which the flexible substrate is at least partially unrolled from the rolled configuration.

Clause 29: The pump assembly of claims 26, 27 or 28, further comprising a battery electronically coupled to the induction coil, the battery being configured to be recharged by power produced by the induction coil.

Clause 30: A pump assembly for inducement of negative pressure in a bladder of a patient, the assembly comprising: a pump module, wherein at least a portion of the pump module is configured to be positioned in a portion of a bladder of a patient, the pump module comprising a housing comprising an open proximal end, an open distal end, and a sidewall extending therebetween, the housing defining a flow channel for conducting fluid through an interior portion of a patient's bladder, and a pump element at least partially positioned within the channel that that is configured to draw fluid through the channel between the open distal end and the open proximal end of the housing; a bladder wall support for maintaining at least a portion of the bladder wall in an un-collapsed state in which ureter orifices are not occluded by the bladder wall; and a drainage catheter extending from the proximal end of the pump module through the urethra and from the patient's body, the drainage catheter comprising a drainage lumen in fluid communication with the channel of the pump module for directing fluid expelled from the pump module from the body.

Clause 31: The pump assembly of claim 30, wherein the bladder wall support comprises an inflatable trigone isolating balloon, comprising a superior surface portion for supporting a superior wall of the patient's bladder and a concave inferior surface portion.

Clause 32: The pump assembly of claim 30 or 31, wherein the trigone isolating balloon has a maximum inflated height of about 5 cm and a maximum inflated width of about 15 cm.

Clause 33: The pump assembly of claims 30, 31 or 32, wherein the drainage catheter further comprises an inflation lumen in fluid communication with an interior of the trigone isolating balloon for providing fluid to an interior of the trigone isolating balloon to inflate the balloon.

Clause 34: The pump assembly of claim 33, wherein the inflation lumen extends through the drainage channel, such that a longitudinal central axis of the drainage channel is substantially co-extensive with a longitudinal central axis of the inflation lumen.

Clause 35: The pump assembly of claims 30, 31, 32, 33 or 34, wherein the pump module housing further comprises a plurality of drainage openings extending therethrough for drawing fluid from the bladder into the flow channel.

Clause 36: The pump assembly of claims 30, 31, 32, 33, 34 or 35, wherein the pump module further comprises an annular filter extending about at least a portion of the housing sidewall and covering one or more of the plurality of drainage openings for filtering fluid as the fluid is drawn into the flow channel.

Clause 37: A pump assembly comprising: (a) a pump module, wherein at least a portion of the pump module is configured to be positioned within at least one of an interior portion of a ureter, an interior portion of a renal pelvis, an interior portion of a bladder, or an interior portion of a urethra of a patient for providing negative pressure to at least one of the patient's ureter or kidney, the pump module comprising: a housing comprising an open proximal end, an open distal end, and a sidewall extending therebetween defining a flow channel for conducting fluid through at least one of the interior portion of the patient's ureter, the interior portion of the patient's bladder, the interior portion of the patient's bladder, or the interior portion of the patient's urethra, wherein at least a portion of the housing comprises a drainage channel comprising a distal portion configured to be positioned within at least one of a distal interior portion of the ureter or the interior portion of the renal pelvis of a patient; a pump element at least partially positioned within the channel configured to draw fluid through the channel between the open distal end and the open proximal end of the housing; and (b) a control module coupled to the pump module, the control module being configured to direct motion of the pump element to control flow rate of fluid passing through the channel, the control module comprising a housing configured to be positioned within a second interior portion of the patient's ureter, a second portion of the patient's renal pelvis, a second interior portion of the patient's bladder, or a second interior portion of the patient's urethra, wherein the drainage channel is formed integrally with the housing or as a separate tube or conduit in fluid connection with the open distal end of the housing.

Clause 38: A system for providing negative pressure therapy to a patient's ureter and/or kidney, the system comprising: a pump assembly, comprising: (a) a pump module, wherein at least a portion of the pump module is configured to be positioned within at least one of an interior portion of a ureter, an interior portion of a renal pelvis, an interior portion of a bladder, or an interior portion of a urethra of a patient for providing negative pressure to at least one of the patient's ureter or kidney, the pump module comprising: a housing comprising an open proximal end, an open distal end, and a sidewall extending therebetween defining a flow channel for conducting fluid through at least one of the interior portion of the patient's ureter, the interior portion of the patient's renal pelvis, an interior portion of the patient's bladder, or the interior portion of the patient's urethra, wherein at least a portion of the housing is configured to be positioned within at least one of the interior portion of the ureter, the interior portion of the renal pelvis, the interior portion of the bladder, or the interior portion of the urethra of a patient; and a pump element at least partially positioned within the channel configured to draw fluid through the channel between the open distal end and the open proximal end of the housing; and (b) a control module coupled to the pump module, the control module being configured to direct motion of the pump element to control flow rate of fluid passing through the channel, the control module comprising a housing configured to be positioned in at least one of a second interior portion of the patient's ureter, a second interior portion of the patient's renal pelvis, a second interior portion of the patient's bladder, or a second interior portion of the patient's urethra; a power supply for providing power to the pump assembly; and a remote control device in wired or wireless communication with the control module, the remote control device being configured to provide instructions to the control module for operating the pump assembly and to receive information from the control module about at least one of the pump module or the patient.

Clause 39: The system of claim 38, wherein a maximum outer diameter of the pump module housing is less than a maximum outer diameter of the control module.

Clause 40: The system of claim 38 or 39, wherein the control module is sized for insertion into the patient's bladder.

Clause 41: The system of claims 38, 39 or 40, wherein the power supply is a battery.

Clause 42: The system of claims 38, 39, 40 or 41, wherein the power supply is an induction coil.

Clause 43: The system of claim 38, wherein the remote control device further comprises an electromagnetic field generator configured to generate an electromagnetic field which, when exposed to the induction coil, causes the induction coil to generate power for operating at least one of the control module or the pump module.

Clause 44: The system of claim 38, wherein the power supply further comprises a battery electronically coupled to the induction coil, the battery being configured to be recharged by power produced by the induction coil.

Clause 45: The system of claim 44, wherein information received from the control device comprises at least one of an indication that the battery is being recharged by the induction coil, an indication that the battery is fully charged, or an indication of a charge remaining of the battery.

Clause 46: The system of claims 38, 39, 40, 41, 42, 43, 44 or 45, further comprising a remote database comprising electronic patient heath records, and wherein the remote control device is configured to wirelessly transmit information about the patient to the remote database.

Clause 47: The system of claims 38, 39, 40, 41, 42, 43, 44, 45 or 46, further comprising sensors in fluid communication with the flow channel of the pump module housing, the sensors being configured to measure a pump operating parameter or a physiological condition of the patient based on sensed information about fluid passing through the flow channel.

Clause 48: The system of claim 38, 39, 40, 41, 42, 43, 44, 45, 46 or 47, wherein the remote control device further comprises a display, and wherein the remote control device is configured to display the information received from the control module about at least one of the pump module or the patient on the display.

Clause 49: A method for treating a patient by providing negative pressure therapy to a portion of the patient's urinary tract, the method comprising: positioning a pump assembly comprising: (a) a pump module, wherein at least a portion of the pump module is configured to be positioned within at least one of an interior portion of a ureter, an interior portion of a renal pelvis, an interior portion of a bladder, or an interior portion of a urethra of a patient for providing negative pressure to at least one of the patient's ureter or kidney, the pump module comprising: a housing comprising an open proximal end, an open distal end, and a sidewall extending therebetween defining a flow channel for conducting fluid through at least one of the interior portion of the patient's ureter, the interior portion of the patient's renal pelvis, the interior portion of the patient's bladder, or the interior portion of the patient's urethra, wherein at least a portion of the housing is configured to be positioned within at least one of the interior portion of the ureter, the interior portion of the renal pelvis, the interior portion of the bladder, or the interior portion of the urethra of a patient; and a pump element at least partially positioned within the channel configured to draw fluid through the channel between the open distal end and the open proximal end of the housing; and (b) a control module coupled to the pump module, the control module being configured to direct motion of the pump element to control flow rate of fluid passing through the channel, the control module comprising a housing configured to be positioned within at least one of a second interior portion of the patient's ureter, a second interior portion of the patient's renal pelvis, ta second interior portion of the patient's bladder, or a second interior portion of a patient's urethra; and activating the pump module thereby causing the pump module to draw fluid through the channel thereof to deliver negative pressure to a portion of the patient's urinary tract.

Clause 50: The method of claim 49, wherein the control module housing is sized for insertion in the patient's bladder, and wherein a maximum external diameter of the pump module is less than the maximum outer diameter of the control module.

Clause 51: The method of claim 49 or 50, wherein the assembly is deployed within a portion of the patient's bladder and/or ureter by use of a catheter.

Clause 52: The method of claims 49, 50 or 51, wherein positioning the pump assembly further comprises deploying retention barbs against an inner wall of the bladder and/or ureter to maintain positioning of the pump assembly within the bladder and/or ureter.

Clause 53: The method of claims 49, 50, 51 or 52, wherein negative pressure is delivered in a range of between 0 and about 150 mmHg.

Clause 54: The method of claims 49, 50, 51, 52 or 53, wherein activating the pump module further comprises periodically reversing pump direction for a period of time to provide intermittent positive pressure to the patient's urinary tract.

BRIEF DESCRIPTION OF THE DRAWINGS

These and other features and characteristics of the present disclosure, as well as the methods of operation, use, and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which:

FIG. 7 is a cross-sectional view of a portion of the pump assembly of FIGS. 2A and 2B taken along line 7-7;

FIG. 8 is a cross-sectional view of a portion of a pump assembly according to an example of the present disclosure;

DETAILED DESCRIPTION

Figure 1A:
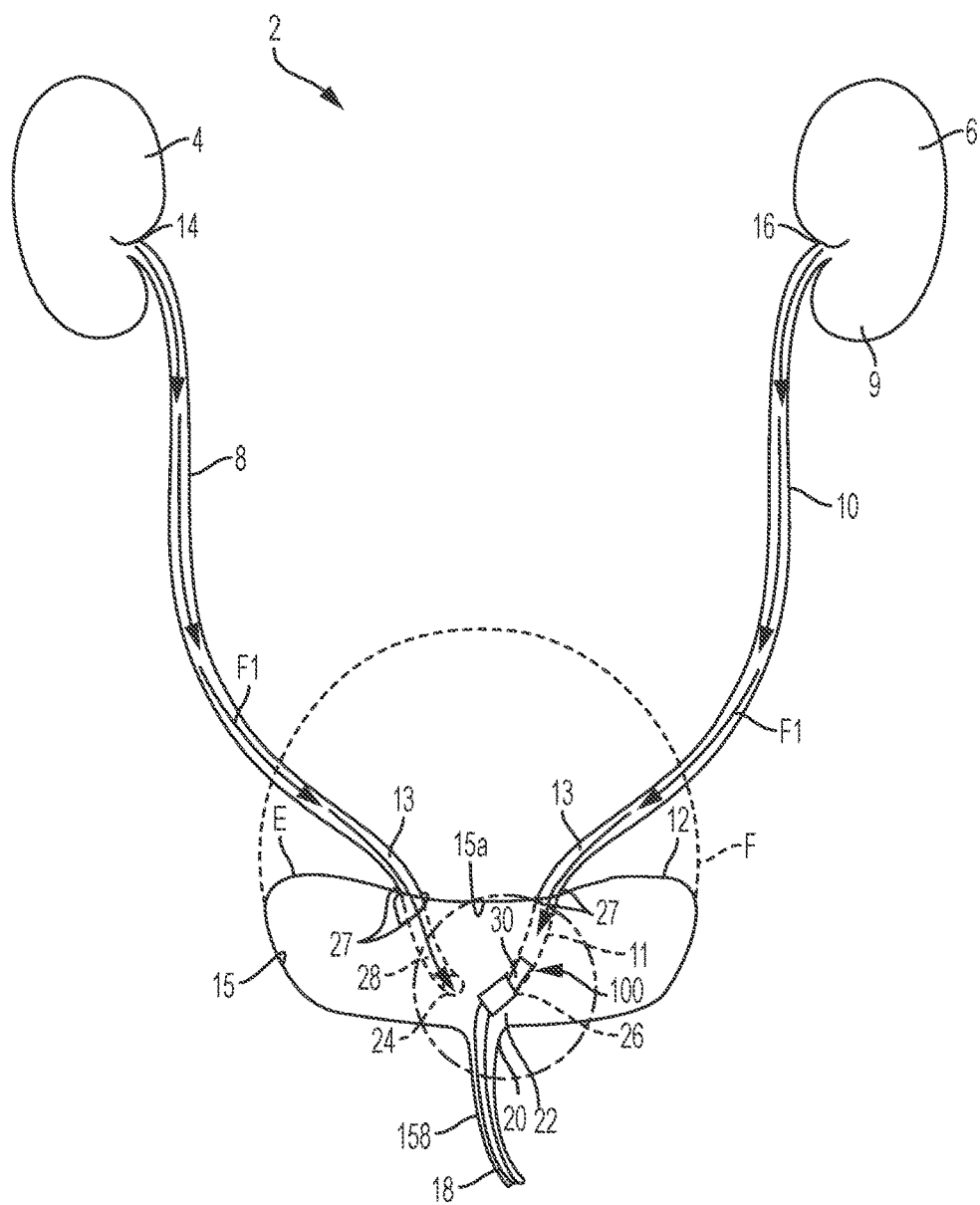
FIG. 1A is a schematic drawing of a urinary tract of a patient showing a pump assembly positioned in the ureter and bladder of the patient according to an example of the present disclosure.
Figure 1B:
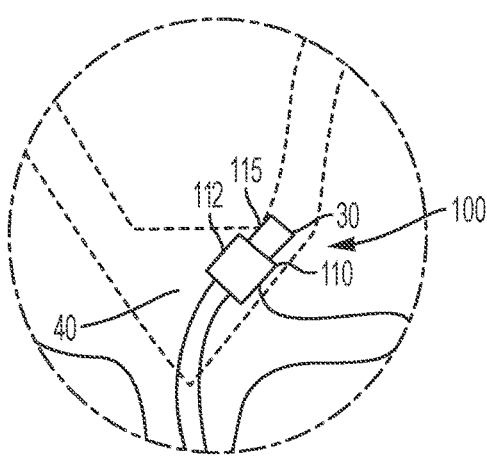
FIG. 1B is an enlargement of a portion of FIG. 1A.
Figure 1C:
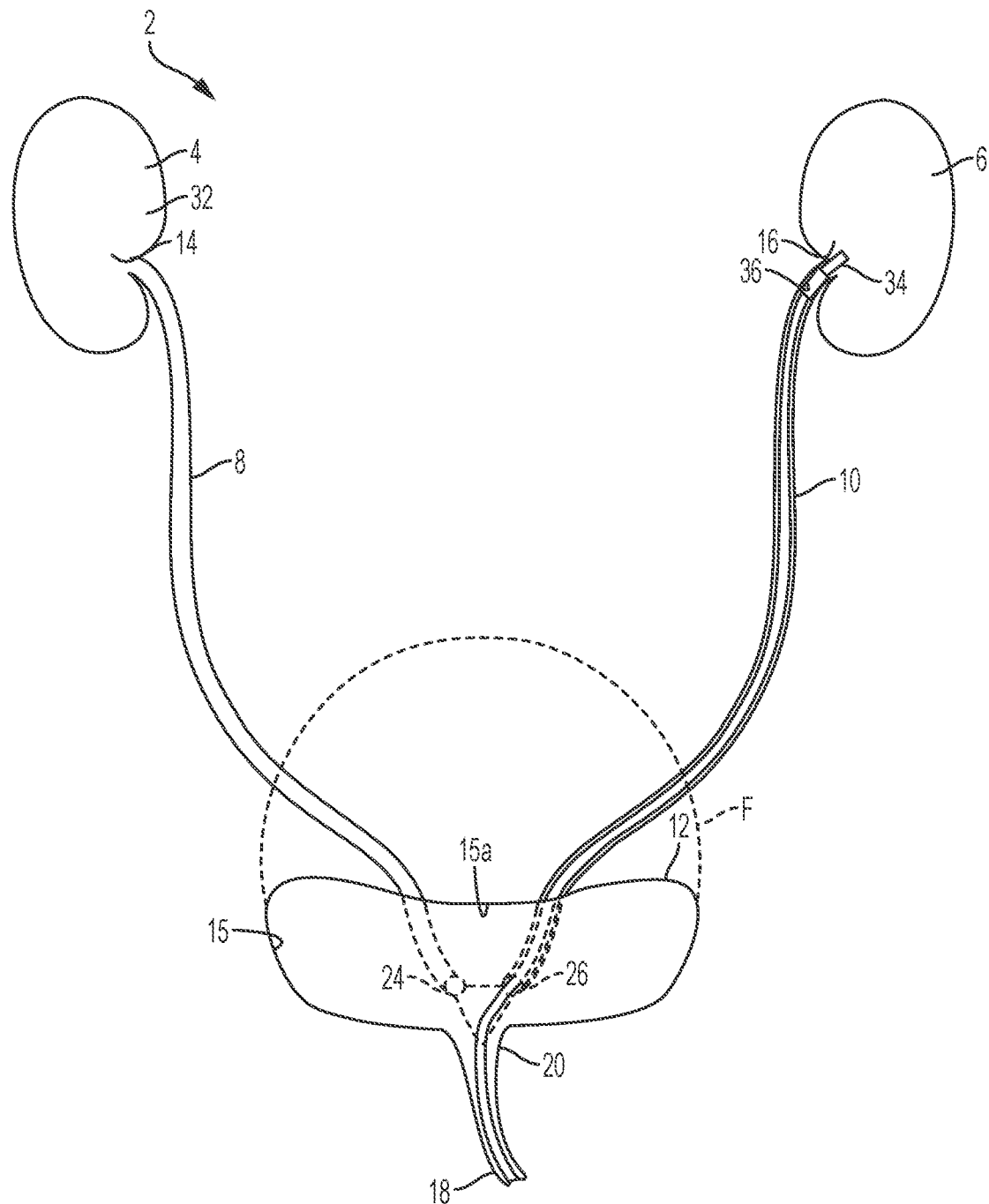
FIG. 1C is a schematic drawing of a urinary tract of a patient showing a pump assembly positioned in the renal pelvis and ureter of the patient according to another example of the present disclosure.
Figure 1D:
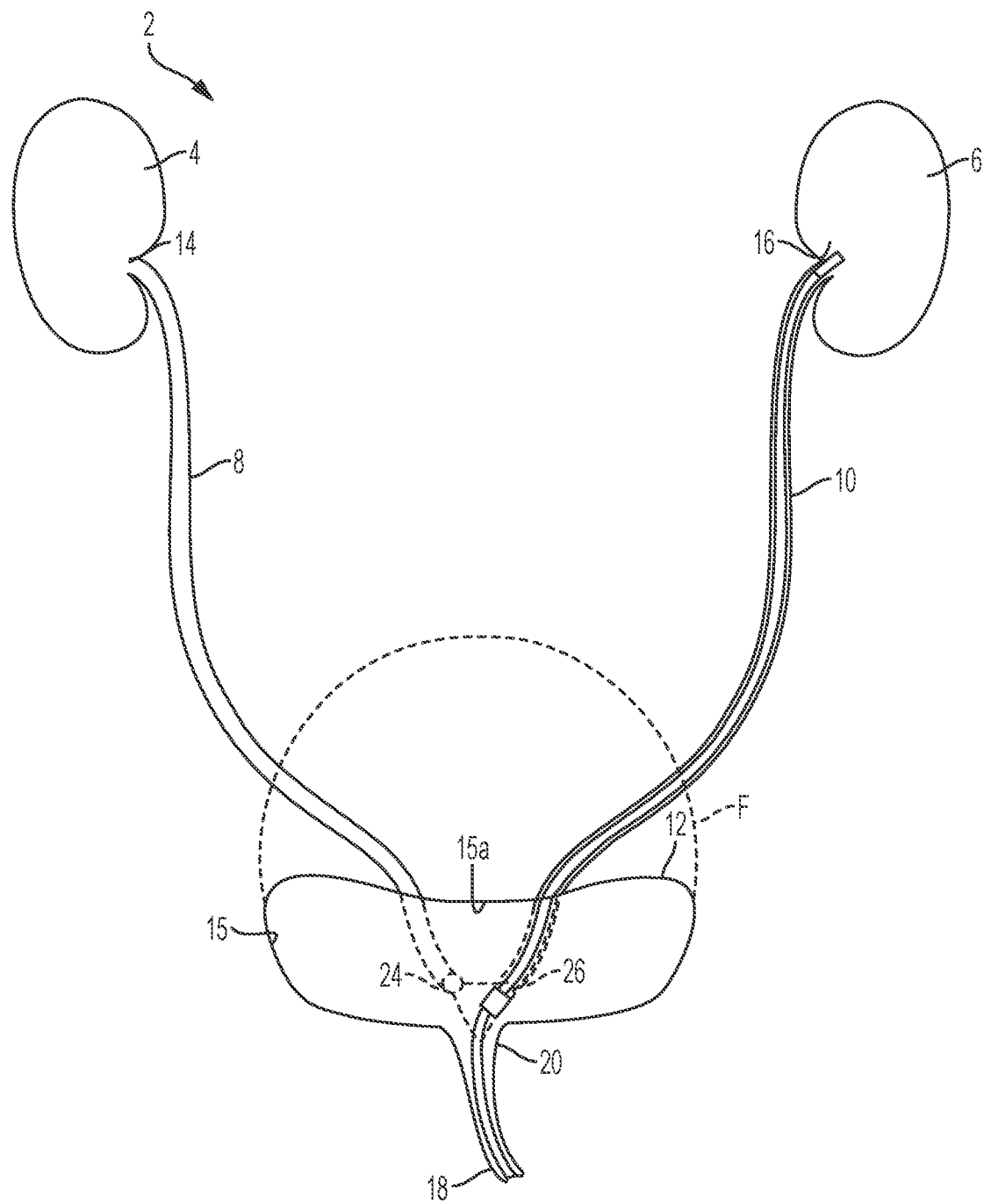
FIG. 1D is a schematic drawing of a urinary tract of a patient showing a pump assembly positioned in the bladder of the patient according to another example of the present disclosure.

As used herein, the singular form of "a", "an", and "the" include plural referents unless the context clearly states otherwise.

As used herein, the terms "right", "left", "top", and derivatives thereof shall relate to the invention as it is oriented in the drawing figures. For a device or system, the term "proximal" refers to a portion of the device or system nearest to the access site through which the device or system is inserted into the body. For an indwelling urinary tract pump, the proximal portion is the portion of the device or system nearest to the urethra. The term "distal" refers to the opposite end of a device or system from the proximal end and, for example, to the portion of the device or system that is inserted farthest into the patient's urinary tract. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Numerical values may inherently contain certain errors resulting from a standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like between the first and second unit or component. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible.

Generally, the pump assemblies, systems and methods of the present disclosure can be used to introduce a negative pressure or a positive pressure in at least a portion of patient's urinary tract to establish a desirable pressure gradient or pressure differential across the filtration anatomy of the nephron, e.g., glomerulus, proximal tubules, and distal tubules. In some examples, the pump assemblies, systems and methods of the present disclosure can be used to provide negative pressure therapy or positive pressure therapy for treatment of medical conditions such as acute or chronic treatment of venous congestion resulting from, for example, heart failure, sepsis, burn, and other primary morbidities impacting renal pressure gradients and nephron filtration. Systems for providing negative pressure therapy are also disclosed in International Publication No. WO 2017/015351 entitled "Ureteral and Bladder Catheters and Methods for Inducing Negative Pressure to Increase Renal Perfusion" and International Publication No. WO 2017/015345 entitled "Catheter Device and Method for Inducing Negative Pressure in a Patient's Bladder", each of which is incorporated by reference herein its entirety.

In some examples, the pump assemblies, systems and methods disclosed herein can be used to treat and/or control fluid retention and venous congestion, which can contribute to conditions such as heart disease, acute kidney injury, and renal failure. For example, fluid retention and venous congestion are known to be central problems in the progression to advanced renal disease. Excess sodium ingestion coupled with relative decreases in excretion lead to isotonic volume expansion and secondary compartment involvement. While not intending to be bound by any theory, it is believed that applying a negative pressure to the bladder, ureter, and/or kidney(s) can offset the medullary nephron tubule reabsorption of sodium and water in some situations. Offsetting reabsorption of sodium and water can increase urine production, decrease total body sodium, and improve erythrocyte production. Since the intra-medullary pressures are driven by sodium and, therefore, volume overload, the targeted removal of excess sodium enables maintenance of volume loss. Removal of volume restores medullary hemostasis. Normal urine production is 1.48-1.96 L/day (or 1-1.4 ml/min).

Fluid retention and venous congestion are also central problems in the progression of prerenal Acute Kidney Injury (AKI). Specifically, AKI can be related to loss of perfusion or blood flow through the kidney(s). Accordingly, in some examples, the present invention facilitates improved renal hemodynamics and increases urine output for the purpose of relieving or reducing venous congestion generally, and for example in the treatment of AKI, heart failure and/or kidney disease. Further, it is anticipated that treatment and/or inhibition of AKI positively impacts and/or reduces the occurrence of other conditions, for example, reduction or inhibition of worsening renal function in patients with NYHA Class III and/or Class IV heart failure. Classification of different levels of heart failure is described in *The Criteria Committee of the New York Heart Association*, (1994),

*Nomenclature and Criteria for Diagnosis of Diseases of the Heart and Great Vessels*, (9th ed.), Boston: Little, Brown & Co. pp. 253-256, the disclosure of which is incorporated by reference herein in its entirety. Reduction or inhibition of episodes of AKI and/or chronically decreased perfusion may also be a treatment for Stage 4 and/or Stage 5 chronic kidney disease. Chronic kidney disease progression is described in National Kidney Foundation, K/DOQI *Clinical Practice Guidelines for Chronic Kidney Disease: Evaluation, Classification and Stratification*. Am. J. Kidney Dis. 39:S1-S266, 2002 (Suppl. 1), the disclosure of which is incorporated by reference herein in its entirety.

Referring now to FIG. 1, a pump or pump assembly according to the present disclosure which is configured or adapted to be placed within a urinary tract of a patient is disclosed herein. A urinary tract, shown generally as 2, of a patient comprises a patient's right kidney 4 and left kidney 6. The kidneys 4, 6 are responsible for blood filtration and clearance of waste compounds from the body through urine. Urine produced by the right kidney 4 and the left kidney 6 is drained into a patient's bladder 12 through tubules, namely, a right ureter 8 and a left ureter 10. For example, urine may be conducted through the ureters 8, 10 by peristalsis of the ureter walls, as well as by gravity. A distal portion 9 of the ureter 8, 10 and/or kidney 4, 6 known as the renal pelvis 14, 16 is a cornucopia-shaped structure extending between the ureter 8, 10 and kidney 4, 6. The ureters 8, 10 enter the bladder 12 through a ureter opening or orifice 24, 26. The bladder 12 is a flexible and substantially hollow structure adapted to collect urine until the urine is excreted from the body. The bladder 12 is transitionable from an empty position (signified by reference line E) to a full position (signified by reference line F). Normally, when the bladder 12 reaches a substantially full state, urine is permitted to drain from the bladder 12 to a urethra 18 through a urethral opening or sphincter 20 located at a lower portion of the bladder 12. Contraction of the bladder 12 can be responsive to stresses and pressure exerted on a trigone region 22 of the bladder 12, which is the triangular region extending between ureteral orifices 24, 26 and the urethral opening or sphincter 20. The trigone region 22 is sensitive to stress and pressure, such that as the bladder 12 begins to fill, pressure on the trigone region 22 increases. When a threshold pressure on the trigone region 22 is exceeded, the bladder 12 begins to contract to expel collected urine through the urethra 18.

Referring now to FIGS. 1A-D and 2A-2B, in some examples, the pump assembly, indicated generally at 100, comprises a pump module 110. At least a portion of the pump module 110 is configured to be positioned within at least one of an interior portion 28, 30 of a ureter 8, 10, an interior portion 32, 34 of a renal pelvis 14, 16, an interior portion 40 of a bladder 12, or an interior portion of a urethra 18 of a patient. For example, the pump module 110 can be configured to be positioned in a proximal portion 11 or a distal portion 9 of a patient's ureter 8, 10 and/or renal pelvis 14, 16. The pump module 110 can be used to provide negative or positive pressure, as desired, to at least one of the patient's ureter 8, 10 or kidney 4, 6.

Figure 2A:
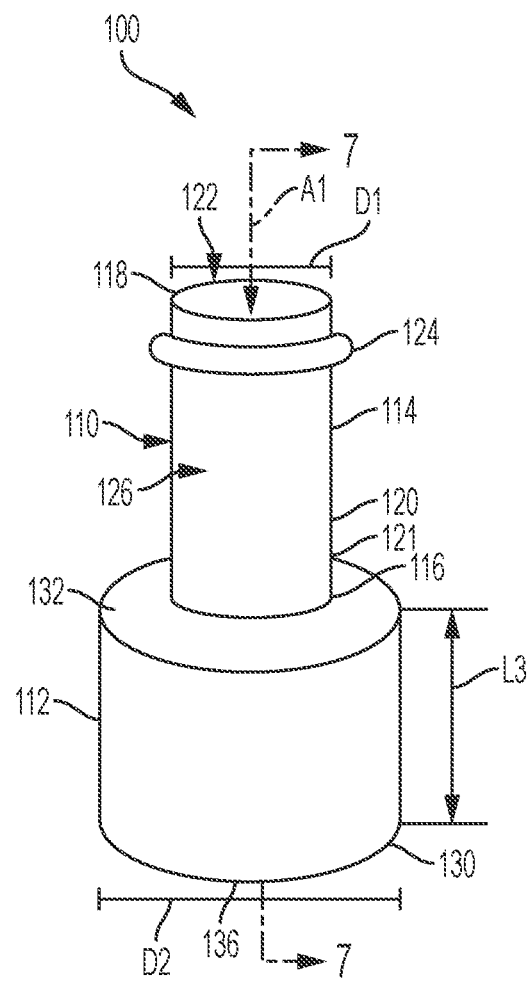
FIGS. 2A and 2B are schematic drawings of a pump assembly according to an example of the present disclosure.
Figure 2B:
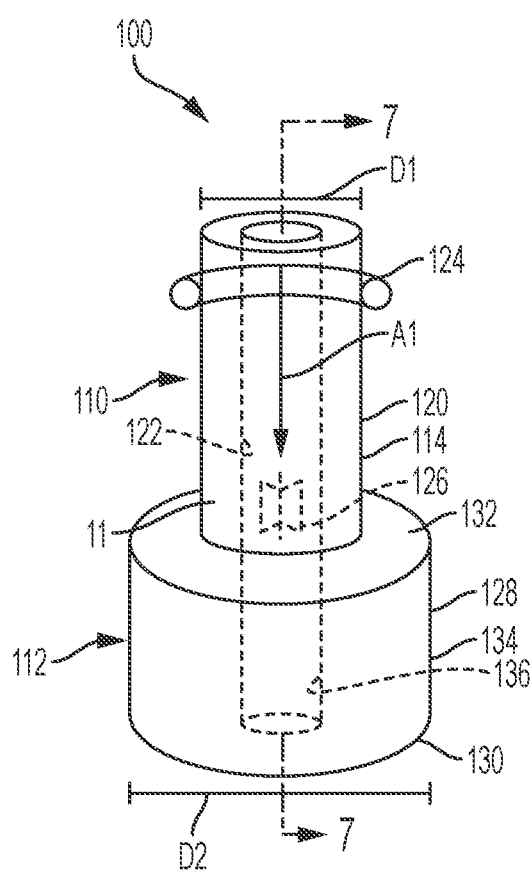

An exemplary pump assembly 100 is shown in FIGS. 2A and 2B. The pump assembly 100 comprises a pump module 110 configured to be positioned within an interior portion 28, 30 (e.g., a proximal portion 11 or distal portion 9) of a ureter 8, 10 and/or an interior portion 32, 34 of a renal pelvis 14, 16 of a patient for providing negative or positive pressure to the patient's ureter and/or kidney, and a control module 112 configured to be implanted and/or deployed in a portion of the ureter 8, 10 and/or renal pelvis 14, 16 or, for example, elsewhere in a patient's urinary tract, for example, in the bladder 12 or the urethra 18.

Pump Module

In some examples, the pump module 110 comprises a housing 114. At least a portion of the housing 114 is configured to be positioned within an interior portion 28, 30 of the ureter 8, 10, an interior portion 32, 34 of the renal pelvis 14, 16, an interior portion 40 of the bladder 12, or an interior portion of the urethra 18. The housing 114 comprises an open proximal end 116, an open distal end 118, and a sidewall 120 extending therebetween, which defines a flow channel 122 for conducting fluid F1 through the interior portion 28, 30 of the patient's ureter 8, 10, the interior portion 32, 34 of the patient's renal pelvis 14, 16, the interior portion of patient's bladder 12, or the interior portion of the patient's urethra 18 (depending upon where the pump module is positioned) and to move the fluid into or through the patient's bladder 12 or urethra 18 to the exterior of the patient. The housing 114 can be formed from one or more suitable biocompatible materials, such as medical grade plastic (e.g., high-density polyethylene, polycarbonates, and silicone materials) and/or metal (e.g., surgical stainless steel).

In some examples, the housing 114 has a maximum external or outer diameter D1 of about 0.5 mm to about 3.0 mm, or about 2.0 mm to about 2.5 mm. The outer diameter D1 can be selected to correspond to an average ureter interior diameter, such that the pump module 110 fits snugly within the ureter.

In some examples, the pump module 110 may at least partially seal the ureter to inhibit bypass leakage of urine and/or to maintain negative pressure. In some examples, the outer cross-section of the housing 114 of the pump module 110 may be sized to fill the interior cross-section of the ureter. The engagement of the tissue of the ureter with the housing 114 at least partially seal the ureter to inhibit bypass leakage of urine and/or to maintain negative pressure. In one example, the housing may be substantially cylindrical and the outer diameter of the housing 114 may be equal to or larger than the interior diameter of the ureter. In some examples as shown in FIG. 2B, in order to facilitate formation of a suitable seal, a flexible and/or resilient elastomeric structure can be positioned about a portion of the exterior of the pump module to at least partially seal the ureter. For example, an annular seal 124 extending around the outer surface 121 of the sidewall 120 circumference of the pump module 110 can be attached to or positioned about a portion of the pump module 110 to form a seal between the housing 114 and the adjacent inner wall 13 of the ureter 8, 10. The seal 124 can be formed from one or more elastomeric biocompatible materials, such as silicone, polyurethane, polyolefin, or hydrogel such as alginate.

The housing 114 can be shaped as desired to facilitate positioning within the ureter, renal pelvis, bladder, or urethra and to accommodate the pump element (discussed below) and flow channel. In some examples, the housing 114 is a substantially cylindrical structure having substantially similar annular cross sections along its entire length. The housing 114 may have a diameter ranging from about 3 mm to about 8 mm or from about 4 mm to about 7 mm and a length ranging from about 5 mm to about 30 mm, from about 10 mm to about 25 mm, or from about 15 mm to about 20 mm. The pump module flow channel may have a diameter ranging from about 1 mm to about 6 mm or about 2 mm to about 5 mm. In other examples, the housing 114 can be tapered to facilitate positioning of distal portions of the housing 114 within the ureters 8, 10, the renal pelvis 14, 16, or the urethra 18. For example, a taper of about 0 to about 6 degrees may be used. In other examples, the housing 114 can have a non-circular cross section. For example, the cross section of the housing 114 can be a square, rectangle, another polygonal shape, or combinations thereof. In some examples, the housing can have a generally smooth outer surface to improve patient comfort.

As discussed in further detail below, to induce negative or positive pressure, the pump module 110 comprises a pump mechanism or element 126 (shown in FIG. 2B) which, while positioned within an interior portion 28, 30 of the ureter 8, 10, an interior portion 32, 34 of the renal pelvis 14, 16, an interior portion 40 of the bladder 12, or an interior portion of the urethra 18 is continuously or periodically activated to draw fluid into a flow channel 122 of the pump module 110, thereby inducing negative or positive pressure in the ureters 8, 10 and/or kidneys 4, 6. The pump element 126 can be at least partially positioned within the channel 122 such that, when activated, draws fluid through the channel 122 between the open distal end 118 and the open proximal end 116 of the housing in the direction of arrow A1. The pump element 126 can operate for a predetermined period of time, for example for a certain period each day, or it can operate continuously. The period of time of pump operation can vary, as desired. The pump element 126 can include different types of molded or machined parts, as are known in the art, including impellers, screw threads, pistons, one-way valves, check valves, and similar structures for drawing fluid through the pump module, as will be described herein. In some examples, the pump element 126 comprises a piezoelectric film or surface which transitions from an extended configuration to a retracted configuration to draw fluid through the pump, such as is described below.

When actuated, the pump module 110 draws fluid F1 (e.g., urine) from the kidney(s) 4, 6 and ureter(s) 8, 10 and moves the fluid F1 to the bladder 12 or through the bladder to outside of the patient's body, thereby inducing a negative pressure in the urinary tract. The rotation or actuation of the pump element 126 can be reversed to provide positive pressure, as needed.

In some examples, fluid F1 is expelled by the pump module 110 into the bladder 12. In other examples, fluid F1 can be conducted through an outlet line 158, such as a tube or conduit, thorough the inside of the urethra 18 and outside the body. The fluid F1 can be collected in a fluid collection container (not shown) located outside of the patient's body. The pump module may be configured to deliver negative pressure in a range of 0 to about 150 mmHg, or about 5 mmHg to about 100 mmHg, or about 10 mmHg to about 50 mmHg. The pump module may be configured to intermittently deliver positive pressure in a range of about 0 to about 150 mmHg, or about 1 mmHg to about 100 mmHg, or about 1 mmHg to about 50 mmHg. The pump module 110 can be configured to provide a volumetric fluid flow rate between 0 and about 3.5 mL/min, between about 0.2 mL/min and about 2.5 mL/min, or between about 0.4 mL/min and about 1.25 mL/min. Generally, the amount of negative or positive pressure delivered by the pump and/or volumetric flow rate is determined from pump operating parameters (e.g., the pump module is set to deliver a predetermined negative pressure or to extract fluid at a predetermined flow rate). However, in some examples, the pump module can comprise pressure sensors for directly or indirectly measuring negative and/or positive pressure exerted on the ureter and/or kidneys by the pump module and/or flow rate sensors for measuring fluid volume drawn through the pump module.

As described herein, negative or positive pressure may be applied continuously or intermittently pulsed to drive continuous or pulsatile flow.

As described herein, the pump element 126 can be, for example, a micro-electrical mechanical component as is known in the art, for example, an Abiomed® Impella® pump or a piezoelectric pump such as those manufactured by Dolomite. Other fabrication techniques for producing components of a pump module 110 configured for insertion in the ureter 8, 10, the renal pelvis 14, 16, or the urethra 18 can comprise, for example, injection molding, three-dimensional printing, metal stamping, and similar fabrication techniques, as are known in the art. For example, as shown in FIGS. 7 and 8, the pump element 126 may comprise an impeller 1 and/or a deformable, a moveable, and/or an expandable piezoelectric element 180. As described in greater detail below with respect to FIG. 11, in some examples, the pump element 126 can be operatively connected to electrical components including a motor (e.g., drive mechanism 228), a power source (e.g., battery 226 and/or induction coil 210), and an on/off switch or controller 218, as well as to different types of optional sensors for measuring pump operating parameters and/or physiological information for the patient, as discussed below.

Pump Element and Associated Electronic Components

Exemplary embodiments of the pump element 126 of the pump module 110 are shown in FIGS. 7 and 8. As discussed previously, the pump element 126 can be positioned at least partially within the channel 122 defined by the pump module housing 114. When activated, the pump element 126 draws fluid, such as urine produced by the kidney, into the channel 122 through the open distal end 118 of the housing 114 and expels the fluid through the open proximal end 116 of the housing 114. In some examples, the pump element 126 may also propel fluid through the channel 136 defined by the control module housing 128 (shown in FIG. 2B) and into the patient's bladder, or through a tube through the bladder and urethra and external to the patient's body.

As shown in FIG. 7, in some examples, the pump element 126 comprises a rotatable impeller 170 positioned within the channel 122. The impeller 170 can be made from various medical-grade materials which are sufficiently strong and rigid to rotate for a prolonged duration without deforming or bending. For example, the impeller 170 can be formed from a metal material, such as surgical stainless steel, and/or from a rigid plastic material, such as polycarbonate. For example, the impeller 170 can comprise two or more blades 172 mounted to and positioned to rotate about a central rotor 174 in a direction of arrow A3. The impeller 170 can have 2 to 4 blades. The blades 173 can have a length of about 8 mm to about 14 mm or about 10 to about 12 mm and a width of about 2 mm to about 3 mm. The clearance between the blades 172 can be about 0.02 mm to about 1 mm or about 0.5 mm to about 0.8 mm. As shown in FIG. 7, the rotor 174 may extend longitudinally through the channel 122 along a central longitudinal axis L4 thereof. The blades 172 may comprise a straight or curved surface 176 configured to contact fluid passing through the channel 122. In some examples, the blades 172 may also be able to rotate about the rotor 174 in an opposite direction to apply positive pressure to the ureter and/or kidney if desired. The blades 172 can have any suitable shape, which when rotated, is capable of drawing fluid through the channel. For example, as shown in FIG. 7, edges 178 of the blades 172 may have a straight, curved or "S"-shaped configuration. As previously discussed, the pump element 126 and impeller 170 can be operatively connected to the drive mechanism or electric motor which, when activated, causes the blades 172 to rotate as described herein.

As shown in FIG. 8, another exemplary pump element 126 comprises a piezoelectric diaphragm 180 configured to transition between a contracted position (shown by dashed lines in FIG. 8) and an expanded position (shown by sold lines in FIG. 8), in which the piezoelectric diaphragm 180 expands into the channel 122 to restrict flow through the channel 122 and reduce a volume and cross-sectional area of the channel 122. The piezoelectric diaphragm 180 can be formed from a thin flexible conductive film, such as a polymer and/or elastomeric film, as is known in the art or from stainless steel. The piezoelectric diaphragm 180 can be electronically coupled to a drive mechanism, such as a signal generator or power source for activating the piezoelectric diaphragm 180. For example, the diaphragm 180 can be activated by passing an electric signal generated by the signal generator or power source through the conductive film of the diaphragm 180 to cause the diaphragm 180 to transition to the extended position. During use, one side of the piezoelectric diaphragm 180 is exposed to the fluid and the drive mechanism is located on the unexposed side of the piezoelectric diaphragm 180. The pump element 126 further comprises valves 182, 184, such as one-way check valves, positioned at the open distal end 118 and open proximal end 116 of the channel 122, respectively, as shown in FIG. 8. The check valves 182, 184 can be conventional one-way valves configured to restrict backflow of fluid, as is known in the art. Exemplary one-way check valve mechanisms can include, for example, a flexible flap or cover, ball valve, piston valve, or similar mechanism.

In operation, fluid is drawn into channel 122 through a distal valve 182 by deflation of the piezoelectric diaphragm 180, as shown by arrow A1 in FIG. 8. For example, a flap 188 of the distal valve 182 may pivot in a direction of arrow A3 to an open position to permit fluid to pass therethrough. As a result of negative pressure produced by deflation or collapsing of the diaphragm 180, the proximal valve 184 is forced to close to prevent backflow of fluid. Once the diaphragm 180 is deflated or collapses by a predetermined amount, motion of the diaphragm 180 is reversed by applying the electric signal to the conductive film. As the diaphragm 180 expands, the distal valve 182 closes to prevent fluid backflow and fluid is expelled from the channel 122 through the open proximal valve 184 through the open proximal end 116 of the housing, into the lower ureter portion 11 and through the urethra 18.

Control Module

The pump assembly 100 further comprises a control module 112 configured to be positioned within at least one of a second interior portion of the patient's ureter 8, 10, a second interior portion of the patient's renal pelvis 14, 16, a second interior portion of the patient's bladder 12, or a second interior portion of a patient's urethra. As used herein, a module can refer to a device in wired or wireless communication with one or more other modules or devices, thereby forming a patient treatment system. In some examples, modules can be portions of a single device or assembly or multiple devices or assemblies and, for example, can be enclosed in a single device housing or multiple housings. In other examples, a module refers to processing circuitry which executes instructions and performs functions based on the executed instructions. In that case, the same processing components may perform functions of different modules. For example, a single controller or microprocessor may be configured to perform both functions of the pump module 110, including actuating and ceasing operation of a pump mechanism or pump element 126, and of the control module 112, such as receiving and processing data transmitted from remote devices.

In some examples, the control module comprises electronic circuitry, such as a controller or microprocessor comprising computer readable memory comprising instructions, that when executed, control pump operating parameters (e.g., flow rate, operating speed, operating duration, etc.). For example, the controller or processor can be configured to output instructions to the pump module to cause the pump module to turn on, turn off, or adjust operating speed. The control module can also comprise one or more communications interfaces for communicating instructions to the pump module and for communicating information about treatment provided to the patient and measured patient parameters to a remote device or data collection facility. For example, the communications interface may be configured to wirelessly transmit data about a patient or treatment provided to a patient to a patient care facility for inclusion in a patient health record.

Figure 3:
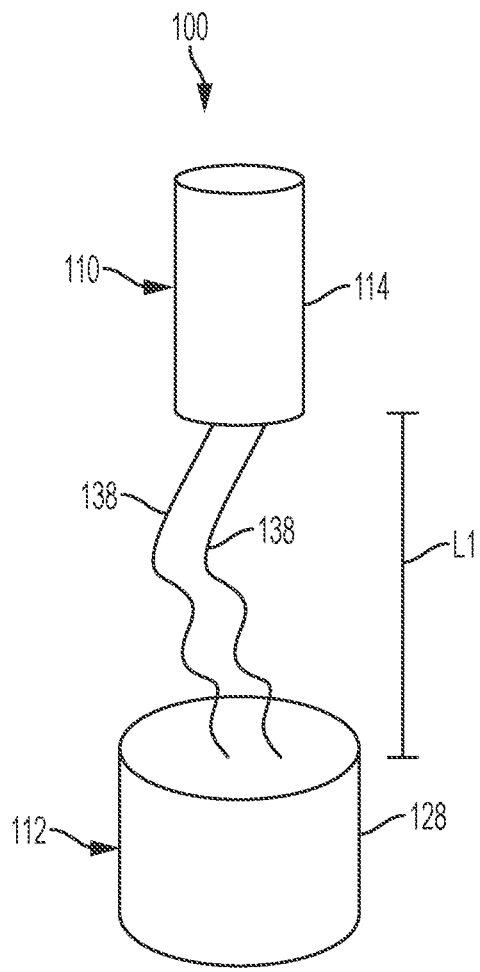
FIG. 3 is a schematic drawing of a pump assembly including a wire linkage between a pump module and a controller module thereof, according to an example of the present disclosure.

The pump module 110 and control module 112 may be integrally formed or directly connected as shown, for example, in FIGS. 2A and 2B. In other examples, separate pump and control modules can be connected by a wireless or wired connection, as shown in FIG. 3. In some examples, the wires extending between the pump module and the control module may extend a substantial portion of the length of the ureter, so that the pump module can be positioned within the renal pelvis region, and the control module can be positioned in the patient's bladder. In other examples, the pump module may be in wireless communication with the control module, which can be spaced apart from the pump module. For example, a remote control device 310, such as a device positioned outside of the patient's body, can be used to control the pump module 110.

The control module 112 is operatively connected to and/or in communication with components of the pump module 110 including the pump element 126 to direct motion of the pump element 126 to control the flow rate of fluid F1 passing through the interior portion of the patient's ureter 8, 10, the patient's renal pelvis, the patient's bladder 12, or the patient's urethra 18.

In some examples, the control module 112 comprises a housing 128. At least a portion of the housing 128 is configured to be positioned within the interior portion 28, 30 of the ureter 8, 10, the interior portion 32, 34 of the renal pelvis 14, 16, the internal portion of the bladder 12, the internal portion of the urethra 18, or elsewhere in the urinary tract 2. The housing 128 comprises a distal end 132, a proximal end 130, and a sidewall 134 extending therebetween. In some examples, the length of the control module 112 can vary, for example the control module 112 can have a length L3 of between about 1 cm to about 5 cm or about 2 cm to about 4 cm. The control module 112 can have a maximum outer diameter D2 which, in some examples, is greater than the maximum outer diameter D1 of the pump module housing 114. The diameter D2 of the control module 112 can vary, for example the control module 112 can have a diameter of between about 5 mm to about 20 mm or about 10 mm to about 15 mm.

The control module housing 128 can be shaped as desired to facilitate positioning within the ureter, the renal pelvis 14, 16, the bladder 12, or the urethra 18, and to accommodate the control module and the flow channel (if present). In some examples, the control module housing 128 is a substantially cylindrical structure having substantially similar annular cross sections along its entire length. In other examples, the control module housing 114 can be tapered to facilitate positioning of distal portions of the control module housing 128 within the ureters 8, 10, the bladder 12, or the urethra 18. For example, a taper of about 0 to about 6 degrees may be used. In other examples, the control module housing 128 can have a non-circular cross section. For example, the cross section of the control module housing 128 can be a square, rectangle, or another polygonal shape.

In some examples, the control module housing 128 is a generally cylindrical structure. The control module housing 128 can optionally comprise a flow channel 136 therethrough. The flow channel 136 can have an inner diameter ranging from about 1 mm to about 6 mm or about 2 mm to about 5 mm. The shape of the interior of the flow channel 136 can have any shape as desired, and in some examples can be generally cylindrical to facilitate flow therethrough. The control module housing 128 can be formed from a similar biocompatible metal or plastic material as the pump module housing 114 described above. In general, the maximum outer diameter D2 can be sufficient to position the control module 112 within the bladder of a patient and, as such, can be wider than the diameter of the ureteral orifice 24, 26 (shown in FIG. 1) and the interior diameter of the ureter so that the control module 112 remains in the bladder and is not drawn into the ureter along with the pump module 110.

Figure 11:
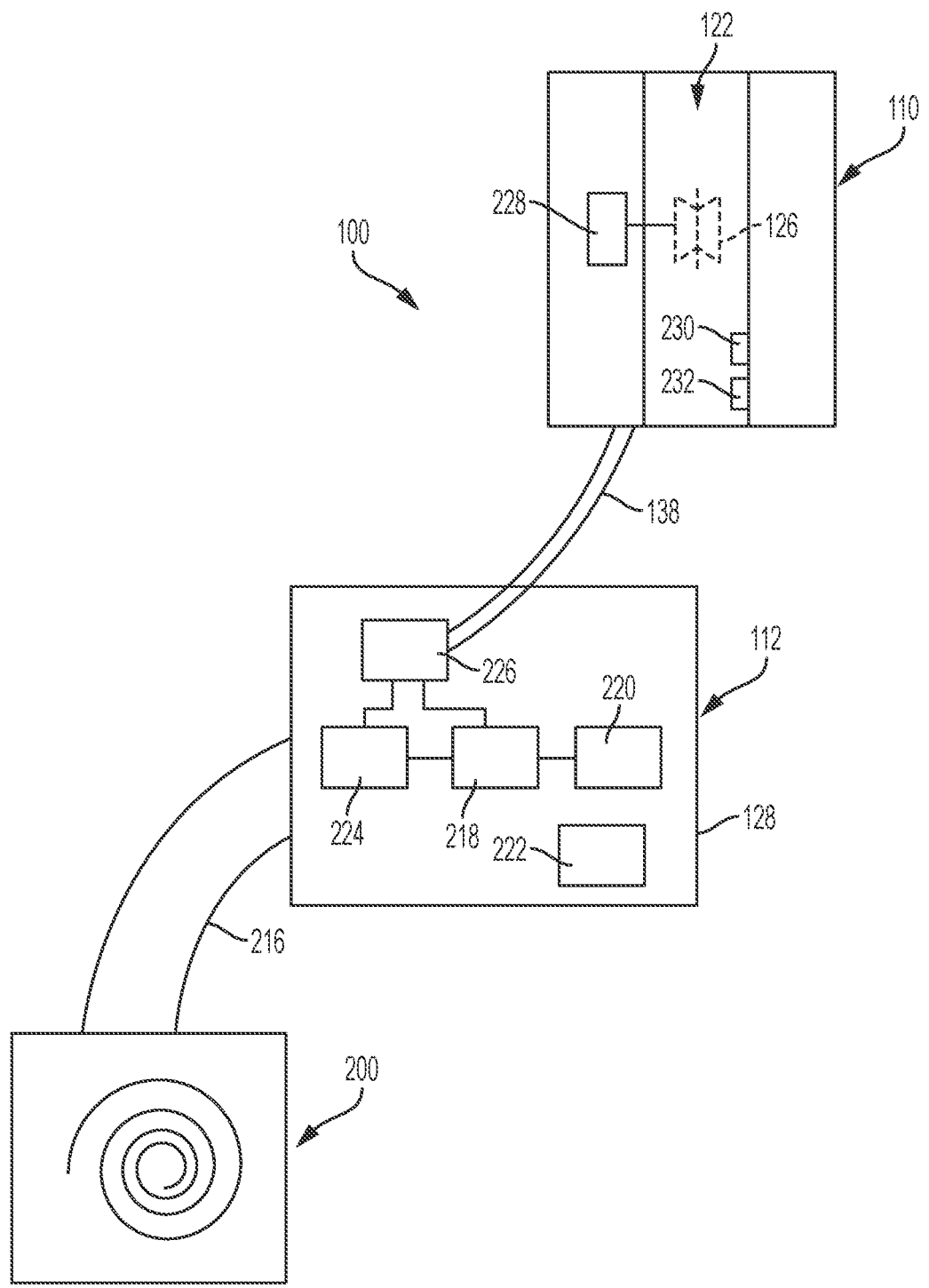
FIG. 11 is a schematic diagram of electronic components of the pump assembly of FIGS. 2A and 2B.

The control module 112 further comprises electronic circuitry for operating the pump element 126, including components for controlling and adjusting pump flow rate, negative and/or positive pressure generated, power usage, and other operating parameters. Exemplary electronic components of the pump assembly 100, including of the control module 112, are shown in FIG. 11 and are described below in detail.

As shown in FIGS. 2A and 2B, in some examples, the pump module 110 and the control module 112 can be integrally formed, such that the respective housings 114, 128 are directly connected to one another. For example, as shown in FIGS. 2A and 2B, the proximal end 116 of the pump module 110 is connected to and/or integrally formed with the distal end 132 of the control module 112. In that case, the channel 122 of the pump module 110 is directly connected to and in fluid communication with the channel 136 of the control module 112, such that fluid F1 is drawn from the ureter 8, 10, the renal pelvis 14, 16, the bladder 12, or the urethra 18 through the flow channel 122 of the pump module 110 and the flow channel 136 of the control module 112, and expelled from the open proximal end 130 of the control module 112 into the patient's bladder or through tubing to conduct the fluid through the bladder 12 and urethra 18 to outside of the patient's body.

As shown in FIG. 3, in another example of a pump assembly 100, the control module housing 128 is separate from the pump module housing 114. In that case, as shown in FIG. 3, the respective modules 110, 112 are connected via a wireless or wired connection formed by one or more wires 138 extending between the respective modules 110, 112. In some examples, the wires 138 are coated with a suitable biocompatible sheath or coating to provide suitable insulation and to facilitate insertion and/or removal of the wires 138 from the urinary track. For example, polymer coatings, such as polyvinyl chloride, polytetrafluoroethylene (PTFE), latex, or silicone may be used. In this example, the control module housing can optionally include the flow channel 136.

The wires 138 can be configured to conduct electronic signals between the modules 110, 112 including, for example, operating instructions from the control module 112 to the pump element 126 of the pump module 110 to control or adjust operating speed and/or to actuate or cease operation of the pump element. Operating parameters and/or information sensed by electronic components of the pump module 110 may be transmitted to the control module 112 via the wired connection for processing, analysis, and/or to be transmitted from the control module 112 to a remote source. In some examples, the wires 138 between the respective modules 110, 112 are rather short in length, meaning that the pump module 110 is configured to be positioned in a proximal portion of the ureter 8, 10, near the ureteral orifice 24, 26 into the bladder 12. In other configurations, the wires 138 are about the length of the ureter, meaning that the pump module 110 can be positioned in the renal pelvis 14, 16 and/or kidney 4, 6, while the control module 112 can be positioned in the ureter 8, 10 and/or the bladder 12. For example, the wires 138 may have a length L1 of about 1 cm to about 35 cm, or about 15 cm to about 25 cm, since the average ureter length of an adult is about 25 cm to about 30 cm.

Power Source

In some examples, the control module 112 further comprises an internal power source or external power source 200 for providing power for the electronic circuitry of the control module 112 and pump element 126 or mechanism of the pump module 110. The power source can be a disposable or rechargeable battery, which, in some examples, may be recharged, for example, using inductive power transfer through a small induction coil deployed, for example, in the bladder. The induction coil may be configured to generate power when exposed to an electromagnetic field generated by a remote device outside of the patient's body. For example, the remote device can be a computerized device, such as a smart phone or tablet PC. In other examples, the remote device can be a non-computerized device including circuitry for generating the electromagnetic field. In one example, a blanket including field generating electromagnetic circuitry can be wrapped around the patient while he/she sleeps. The field generating circuitry can induce the coil to generate power for the entire night or at least until the rechargeable battery is fully charged. Since the patient is less likely to move while sleeping than when awake, it is likely that the portion of the blanket which produces the electromagnetic field remains in close proximity to the pump assembly for a substantial period of time.

Figure 9:
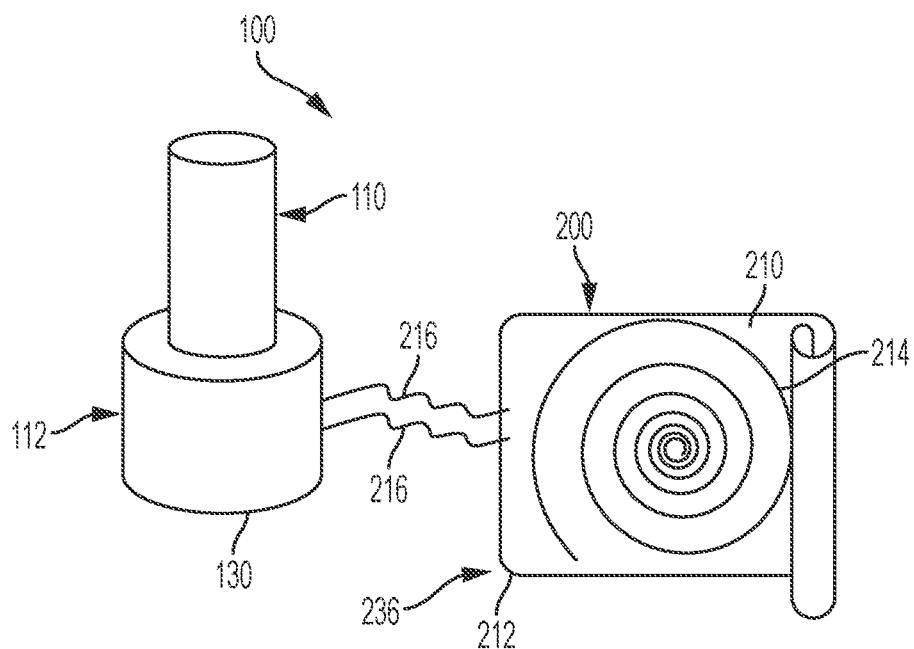
FIG. 9 is a schematic drawing of a pump assembly including a deployable induction coil according to an example of the present disclosure.
Figure 10:
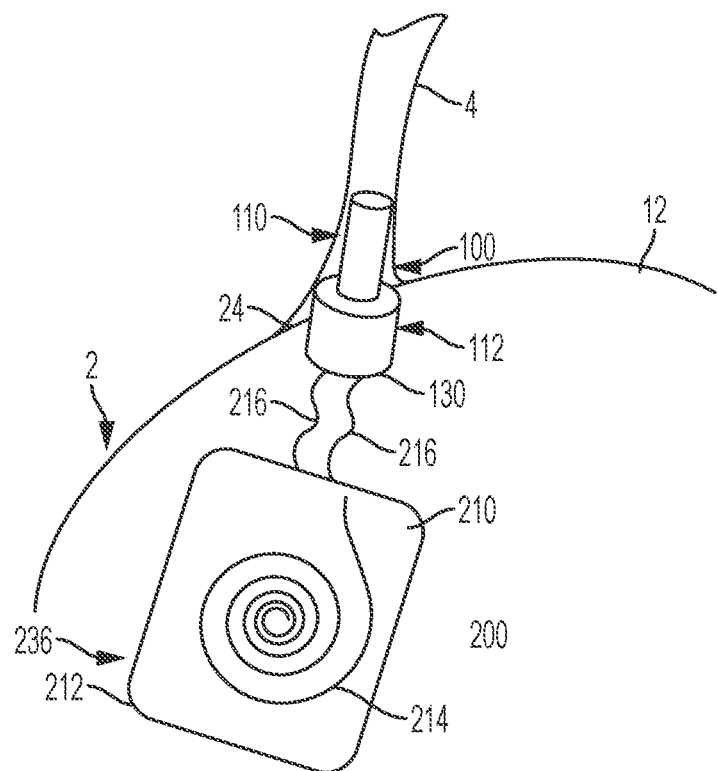
FIG. 10 is a schematic drawing of the pump assembly of FIG. 9 deployed in a patient's urinary tract, according to an example of the present disclosure.

In some examples, the pump assembly 100 further comprises a power source 200, as shown in FIGS. 9 and 10, comprising an induction coil 210 electronically coupled to the pump module 110 and/or to the control module 112. Induction coils for near field wireless energy transfer are known and are used, for example, to charge portable low-power electronic devices such as cell phones, laptop computers, small electrical appliances, and power tools. An exemplary induction coil is the eCoupled system developed by Fulton Innovation, which is described, for example, in U.S. Pat. No. 6,975,198 entitled "Inductive Coil Assembly". Other known or later developed induction systems, which can be positioned in a patient's body and used to generate sufficient power to operate a microelectromechanical device or system may also be used within the scope of the present disclosure.

As described herein, the induction coil 210 generates and provides power to the pump assembly 100 to operate the pump module 110 and control module 112. For example, power produced by the induction coil 210 can be used to recharge a rechargeable battery, to provide power for sensors disposed in the pump module 110, and/or for wireless data transmission between the pump assembly 100 and external devices. In some examples, as discussed herein, the induction coil 210 generates power when exposed to an electromagnetic field produced by another device. For example, the electromagnetic field can be generated by a remote control device 310 (shown in FIG. 12) positioned outside the patient's body. The remote control device 310 can be worn in a holster, carrying case, fanny pack, or pocket, for example, and positioned such that the remote device is held flat against the body and as close as possible to the induction coil 210.

In some examples, shown in FIGS. 9 and 10, the induction coil 210 comprises a flexible sheet 212, such as a polymer sheet, and a conductive wire 214 embedded or attached to the flexible sheet 212. For example, the wire 214 can be attached to the flexible sheet 212 in a spiral pattern, a zig-zag pattern, or any other suitable pattern. The induction coil 210 can be connected to the pump assembly 110 by one or more wires or cables 216. For example, the coil 210 can be connected to the control module 112 through cables 216 extending from the proximal end 130 of the control module 112.

Figure 13A:
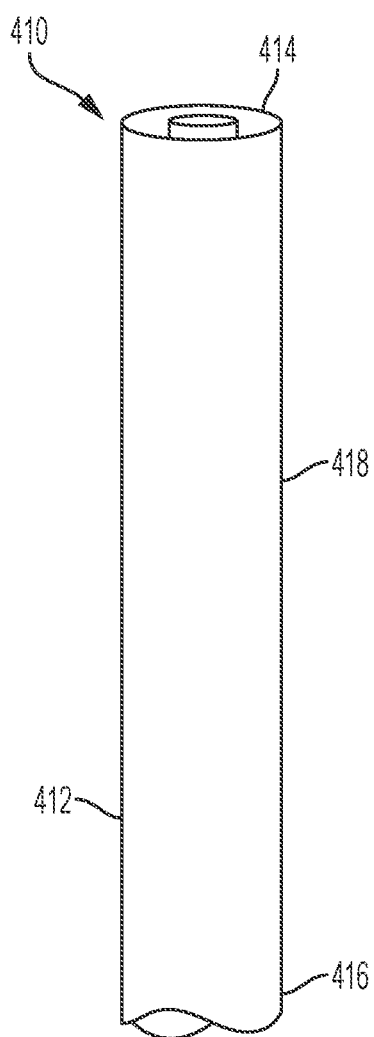
FIG. 13A is a schematic drawing of a delivery catheter for delivery of a pump assembly into a portion of a urinary tract of a patient, according to an example of the present disclosure.
Figure 13B:
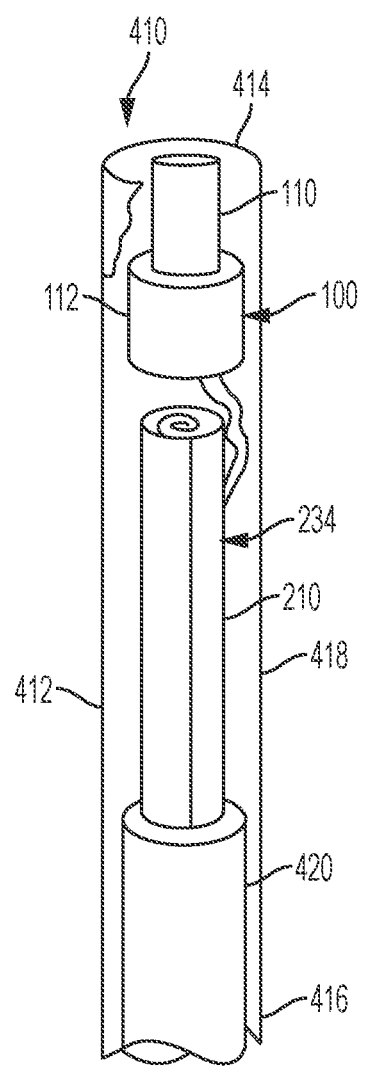
FIG. 13B is a schematic drawing of the delivery catheter of FIG. 13A with portions of an elongated tube cut-away to show the pump assembly contained therein.

In some examples, the flexible sheet 212 is transitionable between a rolled configuration 234 (as shown in FIG. 13B) and an un-rolled or deployed configuration 236 (shown in FIGS. 9 and 10). In some instances, the flexible sheet 212 may be configured to deploy automatically. For example, the sheet 212 may be biased to naturally unroll when it is released from a deployment catheter 410 (shown in FIGS. 13A and 13B). In other examples, the coil 210 may include a manual release mechanism such as a release button or trigger wire. When a user presses the release button or pulls the trigger wire, a latching mechanism for maintaining the coil 210 in the rolled configuration releases allowing the flexible sheet 212 to unroll, thereby transitioning the sheet 212 to the deployed configuration.

The induction coil 210 can be positioned at any convenient position within the patient's urinary tract 2. For example, as shown in FIG. 10, the induction coil 210 can be operatively connected to the control module 112 and is positioned in the patient's bladder 12 at a position proximal to the control module 112. Alternatively, the induction coil 210 may be positioned in the abdominal cavity, outside of the bladder, in the peritoneal cavity, in any other convenient location in vivo, or external to the patient.

Pump Assembly Electrical Components

Exemplary electronic components of the pump assembly 100 are shown in the schematic diagram of FIG. 11. As previously described, the pump assembly 100 comprises the pump module 110, control module 112, and power source, such as induction coil 210 or battery 226 (shown in FIG. 11). The induction coil 210 can be operatively coupled to the control module 112 by cables 216 for proving power to the control module 112.

The control module 112 comprises a controller 218 and associated transitory or non-transitory computer readable memory 220. The controller 218 can comprise, for example, one or more general-purpose microprocessors configured to receive and implement instructions for operating the pump by, for example, communicating with the pump module 110 to actuate or cease operation of the pump element 126 and/or to adjust an operating speed to control negative and/or positive pressure delivered to the patient.

In some examples, the controller 218 can be configured to control communication between the pump assembly 100 and one or more remote control devices 310 located external to the patient. In that case, the control module 112 may further comprise a communications interface 222 comprising, for example, a wireless transmitter or antenna. The communications interface 222 can be configured to receive instructions from a remote source (e.g., remote control device 310) and to emit signals controlling operation of the pump element based on the received instructions.

The control module 112 further comprises power distribution and management circuitry 224. As shown in FIG. 11, the power management circuitry is electrically coupled to the induction coil 210. The power distribution circuitry 224 can be configured to receive power generated by the induction coil 210 and to control distribution of the generated power to other system components.

In some examples, the control module 112 may further comprise a battery 226, such as a rechargeable battery, operatively connected to the controller 218 and power distribution circuitry 224. The battery 226 can be recharged from power generated by the induction coil 210. At times when power is not being generated by the induction coil 210, system components can continue to operate with power provided by the battery 226. The battery 226 can be any battery which is small enough to fit within the control module housing 128 and which has been approved for use in vivo. For example, batteries used in pacemakers and similar implanted devices may be appropriate for use with the pump assembly 100 described herein.

As previously described, electronic components of the control module 112 including the controller 218 are in electronic communication with electrical components of the pump module 110 through, for example, connecting wires 138 (shown in FIGS. 3, 9, and 11) or by another suitable electronic connection. Power generated by the induction coil 210 can be provided to electronic components of the pump module 110 through the wires 138. Additionally, operating instructions generated by the controller 218 can be provided to components of the pump module 110 to control pump operating parameters. In a similar manner, information collected or generated by components of the pump module 110 can be communicated to the controller 218 for further processing and/or to be transmitted wirelessly to a remote device.

As shown in FIG. 11, the pump module 110 comprises the pump element 126 and associated electronic components. For example, the pump module 110 can comprise a drive mechanism 228, such as an electric motor or signal generator, operatively connected to the pump element 126. A variety of different drive mechanisms can be used in connection with the pump module 110 depending on the type of pump element 126 being used. For example, for an impeller-type pump arrangement (as shown in FIG. 7), the drive mechanism 228 may comprise an electric motor which causes the impeller to rotate. In other examples, the drive mechanism 228 can comprise electromagnetic elements disposed around the impeller 170, which turn on and off in a predetermined pattern to cause the impeller to rotate at a desired speed. If the pump element 126 is a piezoelectric element 180, then the drive mechanism 228 can comprise a signal generator for generating electric current to transition the piezoelectric element between the contracted and expanded states.

In some examples, the pump module 110 can further comprise one or more sensors (e.g., pump sensors 230 and physiological sensors 232) positioned within the flow channel 122 of the pump module 110 for measuring information about pump operating conditions and/or about fluid passing through the channel 122. For example, pump sensors 230 can comprise flow sensors for confirming that fluid is passing through the channel 122 and/or for measuring flow rate. Pump sensors 230 can also comprise sensors for measuring an amount of negative and/or positive pressure generated or a pump impeller rotation speed. Physiological sensors 232 can comprise one or more sensors for measuring information about fluid passing through the channel 122 to determine information about the physiological condition of the patient. Exemplary physiological sensors 232 can comprise, for example, capacitance and/or analyte sensors for measuring information representative of chemical composition of generated urine, pH sensors for measuring acidity of urine, or temperature sensors for measuring urine temperature.

Retention Members

Figure 4:
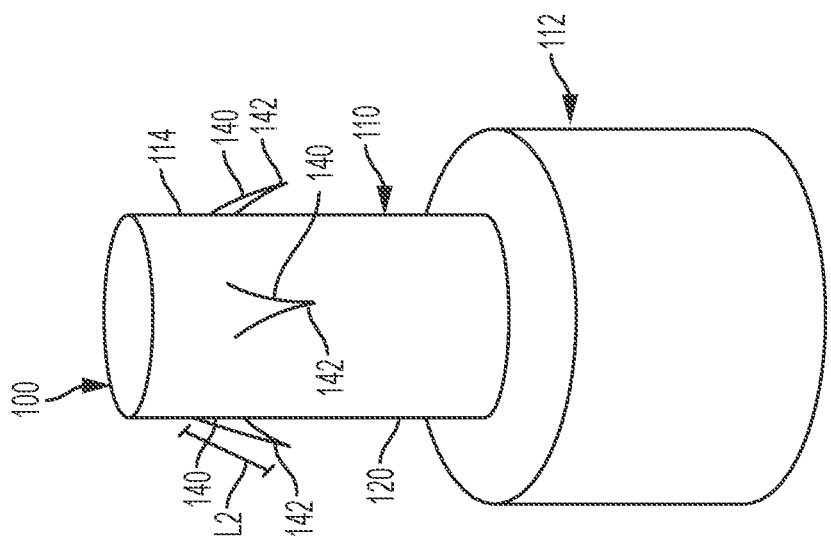
FIG. 4 is a schematic drawing of a pump assembly including anchor barbs extending radially outward from a sidewall thereof, according to an example of the present disclosure.

In some examples, and as shown in FIG. 4, the pump assembly 100 can further comprise one or more retention members, for example retention barbs 140, and/or spiral barbs 144, for maintaining position of the pump module 110 and/or control module 112 within the patient's urinary tract 2. In some examples, the pump module housing 114 and/or control module housing 128 comprises one or more retention members extending from the sidewall for releasably attaching a portion of the pump module housing 114 to at least one of the interior portion of the ureter, the interior portion of the renal pelvis, the interior portion of the bladder, or the interior portion of the urethra of a patient. The retention members are retractable to permit removable of the pump module from the ureter, renal pelvis, the bladder, or the urethra.

In some examples, retention members or retention barbs 140, 144 can be formed in any suitable pattern or arrangement including straight ridges, curved ridges, sharpened protrusions, fish hooks, and combinations thereof. For example, the retention barbs 140 can be deployable and retractable. In that case, the barbs 140 may be in a retracted position as the pump assembly 100 is being advanced through the urinary tract. Once the pump assembly 100 is advanced to a desired position, the barbs 140 are deployed to engage portions of the ureter, renal pelvis, bladder or urethra wall to hold the pump assembly 100 in a desired position. For example, as shown in FIG. 4, an exemplary pump assembly 100 comprises one or more barbs 140 extending radially outward from the sidewall 120 of the pump module 110. The barbs 140 may be flat so that the barbs 140 can be compressed against the sidewall 120 of the housing 114 of the pump module 110 to disengage the tissue of the ureter, renal pelvis, bladder or urethra during removal of the pump assembly 100. Alternatively, the barbs 140 can have any suitable configuration or cross sectional shape including a triangle, circle, semi-circle, rectangle, trapezoid, or polygon. The barbs 140 may have a longitudinal length L2 that may be at least about 0.25 mm or at least about 0.45 mm and may be up to about 3.0 mm, up to about 2.5 mm, or up to about 1.5 mm. The barbs 140 may have a width or diameter of about 1.0 mm or less, about 0.8 mm or less, or about 0.5 mm or less. Prior to insertion, the barbs 140 may extend a maximum distance from the sidewall 120 of the pump module 110 a distance of about 1.0 mm or less, about 0.8 mm or less, or about 0.5 mm or less. The barbs 140 can be formed from a semi-rigid or rigid material suitable for maintaining positioning of the pump module 110 in the urinary tract. For example, the barbs 140 can be formed from metal (e.g., surgical stainless steel) or plastic. The barbs 140 may comprise a sharpened tip 142 for pressing against and slightly encroaching into the ureter, renal pelvis, bladder, or urethra wall to maintain positioning of the pump module 110, without perforating the ureteral wall. Ureteral wall thickness is about 0.05 mm to 0.1 mm, so the tips 142 of the barbs 140 should encroach into the ureter, renal pelvis, bladder, or urethra wall by less than that amount.

In some examples, the barbs 140 are retractable. For example, barbs 140 can be biased in a radially outward direction toward the ureter, renal pelvis, bladder, or urethra wall, but configured to retract against the sidewall 120 of the pump module housing 114 when the pump assembly 100 is being advanced through a deployment catheter and into the patient's ureter, renal pelvis, bladder, or urethra. Once in a deployed position, the barbs 140 may be configured to extend radially outward to a deployed configuration, as shown in FIG. 4. In other examples, the barbs 140 can be extended or retracted by a manually activated triggering mechanism. For example, a user may press a retraction button or pull on a triggering wire to remove a radial biasing force from the barbs 140 to cause the barbs 140 to retract. After the barbs 140 retract, the pump assembly 100 can be safely and easily removed from the urinary tract. For example, the pump module 110 and control module 112 can be removed through the bladder and the urethral sphincter and then from the body through the urethra.

Figure 5:
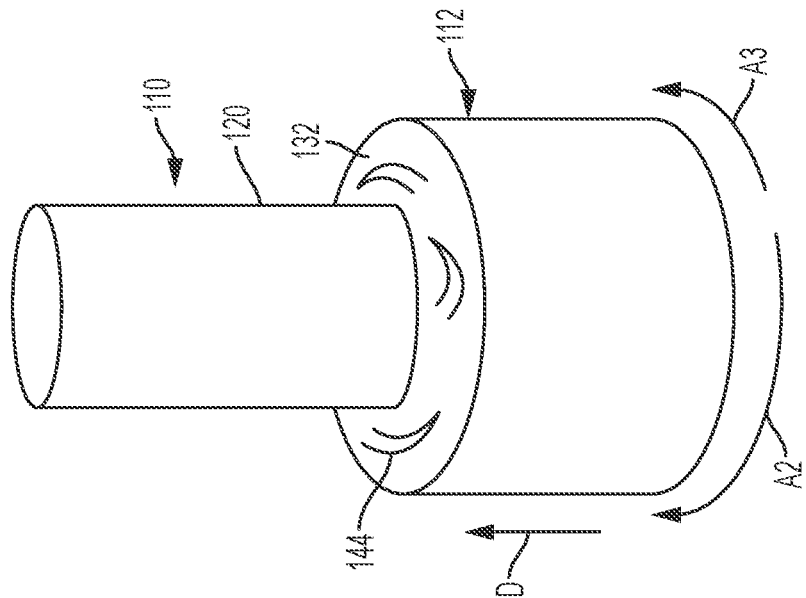
FIG. 5 is a schematic drawing a pump assembly including spiral retention barbs, according to an example of the present disclosure.

In some examples, the control module 112 comprises one or more retention members or barbs 144 for anchoring or retaining the control module to an interior surface of the bladder wall, in addition to or in lieu of the retention members on the pump module. The barbs 144 can be similar to those discussed above for barbs 140. For example, as shown in FIG. 5, retention barbs 144, such as spiral retention barbs, extend in a distal direction D from the distal end 132 of the control module 112. When positioned in the bladder 12, the barbs 144 are configured to contact portions 27 of the bladder wall 15 around the ureter orifice 24, 26 to secure the control module 112 to the bladder wall 15. For example, barbs 144, such as spiral retention barbs, may engage with the bladder wall with a twisting maneuver in a direction shown by arrow A2 (shown in FIG. 5). The spiral barbs 144 may be removed from the bladder wall by twisting the control module 112 in an opposite direction, as shown by arrow A3. In some examples, the spiral barbs 144 can be retractable. In that case, a user may advance the pump assembly 100 into the urinary tract with the proximal end of the control module 112 in contact with the bladder wall. Once the control module 112 is in place, the user deploys the barbs 144 such that the barbs 144 embed into the bladder wall to maintain positioning of the control module 112 and/or pump module 110 within the urinary tract.

Pump Module with Inlet Line

Figure 6:
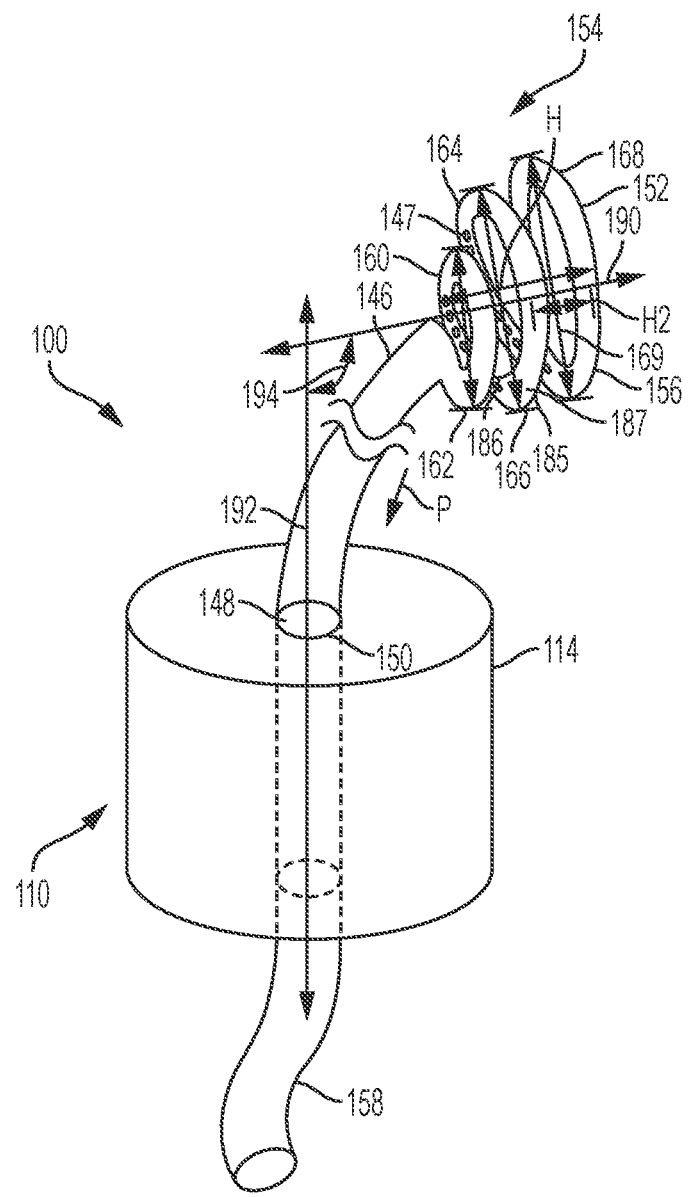
FIG. 6 is a schematic drawing of a pump assembly including an inlet conduit configured to be inserted into a patient's ureter, according to an example of the present disclosure.

In other examples, as shown in FIG. 6, the pump module 110 can be configured to be positioned in the patient's bladder 12 rather than in the ureter 24, 26. In that case, the housing 114 may be large enough to also enclose electronic components of the control module, such as a computer processor and battery. In such a configuration, the pump assembly 100 can further comprise an inlet line 146 or drainage lumen or channel extending from the pump module 110 into the patient's ureter 8, 10 and/or renal pelvis 14, 16. For example, the inlet line 146 can be a substantially tubular conduit comprising a proximal end 148 mounted to a fluid inflow port 150 of the pump module 110 and a distal end 152 for placement in the ureter 8, 10 and/or renal pelvis 14, 16. In some examples, the inlet line 146 can have an external diameter ranging from about 0.33 mm to about 3.0 mm, or about 1.0 mm to 2.0 mm. In some examples, the internal diameter of the inlet line 146 can range from about 0.165 mm to about 2.39 mm, or from about 1.0 mm to 2 mm, or about 1.25 mm to about 1.75 mm. In one example, the inlet line 146 is 6 Fr and has an outer diameter of 2.0±0.1 mm. The inlet line 146 can be formed from one or more suitable biocompatible materials, such as materials used for conventional urinary tract catheters. Exemplary materials can comprise polyvinyl chloride, polytetrafluoroethylene (PTFE) such as Teflon®, silicone coated latex, and/or silicone.

In some examples, the inlet line 146 comprises a plurality of openings 147 or drainage holes extending through a sidewall thereof for drawing fluid from the ureter and/or kidney into an interior lumen or flow channel of the line 146. In other examples, portions of the inlet line 146 can be formed from a porous and/or water absorbent material, such as a sponge, mesh, woven fiber, or similar material. In that case, fluid can be drawn into the interior of the lumen or flow channel through the porous material.

In some examples, the distal end 152 of the inlet line 146 comprises a retention portion, indicated generally at 154, for maintaining the position of the inlet line 146 at a desired fluid collection position proximate to or within the ureter 8, 10 and/or renal pelvis 14, 16. Non-limiting examples of suitable retention portions are disclosed in U.S. Patent Application Publication Nos. 2017/0021128 and 2017/0021129, and PCT International Publication No. WO 2017/015345, each of which is incorporated by reference herein in its entirety.

In some examples, the retention portion 154 is configured to be flexible and bendable to permit positioning of the retention portion 154 in the ureter and/or renal pelvis. The retention portion 154 is desirably sufficiently bendable to absorb forces exerted on the inlet line 146 and to prevent such forces from being translated to the ureters. For example, if the retention portion 154 is pulled in the proximal direction P (shown in FIG. 6) toward the patient's bladder, the retention portion 154 can be sufficiently flexible to begin to unwind or be straightened so that it can be drawn through the ureter. Similarly, when the retention portion 154 can be reinserted into the renal pelvis or other suitable region within the ureter, it can be biased to return to its deployed configuration.

In some examples, the retention portion 154 is integral with the inlet line 146. In that case, the retention portion 154 can be formed by imparting a bend or curl to the inlet line 146 that is sized and shaped to retain the retention portion at a desired fluid collection location. Suitable bends or coils can include a pigtail coil, corkscrew coil, and/or helical coil. For example, the retention portion 154 can comprise one or more radially and longitudinally extending helical coils configured to contact and passively retain the inlet line 146 within the ureter 8, 10 proximate to or within the renal pelvis 14, 16. In other examples, the retention portion 154 is formed from a radially flared or tapered portion of the inlet line 146. For example, the retention portion 154 can further comprise a fluid collecting portion, such as a tapered or funnel-shaped inner surface. In other examples, the retention portion 154 can comprise a separate element connected to and extending from the inlet line 146.

Referring now to FIG. 6, exemplary retention portions 154 comprise a plurality of helical coils, such as one or more full coils and one or more half or partial coils, are illustrated. The retention portion 154 can be capable of moving between a contracted position and the deployed position with the plurality of helical coils. For example, a substantially straight guidewire can be inserted through the retention portion 154 to maintain the retention portion 154 in a substantially straight contracted position. When the guidewire is removed, the retention portion 154 can transition to its coiled configuration. In some examples, the coils 156 extend radially and longitudinally at the distal portion 152 of the inlet line 146. In some examples, the retention portion 154 can comprise one or more coils 156, each coil having an outer coil diameter sufficient to contact at least a portion of the interior wall of the ureter and/or renal pelvis to maintain the inlet line 146 at a desired position in the patient's ureter and/or renal pelvis.

In some examples, the coiled retention portion comprises at least a first coil 160 having a first outer diameter 162; at least a second coil 164 having a second outer diameter 166, the first outer diameter 162 being less than the second outer diameter 166, the second coil 164 being closer to an end of the distal portion of the drainage channel than the first coil 160. The first outer diameter 162 can range from about 12 mm to about 16 mm, or about 13 mm to about 15 mm. The second outer diameter 166 can range from about 16 mm to about 20 mm, or about 17 mm to about 19 mm. The retention portion can further comprise a third coil 168 extending about the axis of the retention portion, the third coil 168 having an outer diameter 169 greater than or equal to either the first coil outer diameter 162 or the second coil outer diameter 166, the third coil 168 being closer to an end of the distal portion of the drainage channel than the second coil 164. The third outer diameter 169 can range from about 12 mm to about 20 mm. The coiled retention portion 154 can have a height H ranging from about 14 mm to about 18 mm.

In some examples, prior to insertion or after insertion into the patient's body, the central axis 190 of the retention portion 154 can be coextensive with, generally parallel to, curved or angled relative to the central axis 192 of the flow channel of the drainage lumen. In some examples, at least a portion of the axis 190 of the retention portion 154 extends at an angle 194 from the central axis 192 from 0 to about 90 degrees, or about 15 degrees to about 75 degrees, or about 45 degrees.

In some examples, prior to insertion into a patient's urinary tract, a portion of the drainage channel that is proximal to the retention portion defines a straight or curvilinear central axis, and wherein, when deployed, the coil(s) of the retention portion extend about the central axis 190 of the retention portion 154 that is at least partially coextensive or coextensive with the straight or curvilinear central axis 192 of the portion of the flow channel 122.

In some examples, multiple coils 156 can have the same inner and/or outer diameter D and height H. In that case, the outer diameter 162, 166, 169 of the coils 156 can range from about 10 mm to about 30 mm. The height H2 between the centerline of each coil 156 can range from about 3 mm to about 10 mm.

In some examples, the retention portion 154 is configured to be inserted in the tapered portion of the renal pelvis. For example, the outer diameter D of the coils 156 can increase toward the distal end 152 of the inlet line 146, resulting in a helical structure having a tapered or partially tapered configuration. For example, the distal or maximum outer diameter 169 of the tapered helical portion ranges from about 10 mm to about 30 mm, which corresponds to the dimensions of the renal pelvis.

In some examples, the outer diameter 162, 166, 169 and/or height H2 of the coils 156 can vary in a regular or irregular fashion. For example, the outer diameter 162, 166, 169 of coils or height H2 between coils can increase or decrease by a regular amount (e.g., about 10% to about 25% between adjacent coils 156). For example, for a retention portion 154 having three coils (as shown, for example, in FIG. 6) an outer diameter 162 of a proximal-most coil or first coil 160 can range from about 6 mm to about 18 mm, an outer diameter 166 of a middle coil or second coil 164 can range from about 8 mm to about 24 mm, and an outer diameter 169 of a distal-most or third coil 168 can range from about 10 mm to about 30 mm.

Other non-limiting examples of suitable retention portions, such as funnel-shaped structures, inflatable or balloon structures, porous and/or sponge-like structures, and expandable cage structures are disclosed in U.S. Patent Application Publication Nos. 2017/0021128 and 2017/0021129, and PCT International Publication No. WO 2017/015345, incorporated by reference herein. Some examples of suitable catheters, systems and methods of use are disclosed in U.S. patent application Ser. No. 15/687,064, entitled "Ureteral and Bladder Catheters and Methods of Inducing Negative Pressure to Increase Renal Perfusion", filed on Aug. 25, 2017, which is incorporated by reference herein in its entirety.

Optionally, the retention portion 154 can further comprise one or more perforations or drainage holes 147 configured to draw fluid into an interior of the inlet line 146, for example disposed on or through the sidewall of the inlet line 146 on or adjacent to the retention portion 154 to permit urine waste to flow from the outside of the inlet line 146 to the inside of the flow channel. Drainage holes 147 can be positioned in a spaced apart arrangement along a sidewall of the inlet line 146. In some examples, the retention portion 154 can further comprise an additional hole at a distal end 152 of the retention portion 154.

The drainage holes 147 can be located, for example, proximate the open distal end 152 of the inlet line 146. In other examples, perforated sections and/or drainage holes 147 are disposed along the sidewall 185 of the distal portion of the inlet line 146. The drainage holes 147 can be used for assisting in fluid collection. In other examples, the retention portion 154 is solely a retention structure and fluid collection and/or imparting negative pressure is provided by structures at other locations on the inlet line 146.

In some examples, the retention portion 154 of the inlet line 146 comprises a sidewall 185 comprising a radially inwardly facing side 186 and a radially outwardly facing side 187, and wherein a total surface area of perforations or holes 147 on the radially inwardly facing side 186 is greater than a total surface area of perforations or holes 147 on the radially outwardly facing side 187. In some examples, the radially outwardly facing side 187 is essentially free or free of perforations.

The configuration of the drainage holes 147 can be any configuration which permits the passage of fluid F1 therethrough, such as circular or non-circular. The position and size of the drainage holes 147 can vary depending upon the desired flow rate and configuration of the retention portion. The diameter of each of the drainage holes 147 can range from about 0.05 mm to 1.1 mm, about 0.7 mm to about 0.9 mm. The cross-sectional area of each drainage hole 147 ranges from about 0.002 mm$^2$ to about 1.0 mm$^2$, or about 0.35 mm$^2$ to about 0.65 mm$^2$. The distance between adjacent drainage holes 147, for example the linear distance between drainage holes 147 when the coils are straightened, can range from about 20 mm to about 25 mm, or about 21 mm to about 23 mm. The drainage holes 147 can be spaced in any arrangement, for example, linear or offset. The total cross-sectional area of all of the drainage holes 147 can range from about 0.002 mm$^2$ to about 10 cm$^2$, about 0.02 mm$^2$ to about 8 cm$^2$, or about 0.2 mm$^2$ to about 5 cm$^2$. In some examples, the drainage holes 147 can be non-circular, and can have a cross-section area of about 0.00002 mm$^2$ to about 0.79 mm$^2$ or about 0.02 mm$^2$ to about 0.8 mm$^2$.

In some examples, the drainage holes 147 are located around the entire periphery of the sidewall of the inlet line 146 to increase an amount of fluid that can be drawn into the flow channel. In other examples, the drainage holes 147 can be disposed essentially only on the radially inwardly facing side 186 of the coils 156 to prevent occlusion or blockage of the drainage holes 147, and the outwardly facing side 187 of the coils may be essentially free of drainage holes 147. For example, when negative pressure is induced in the ureter and/or renal pelvis, mucosal tissue of the ureter and/or kidney may be drawn against the retention portion 154 and may occlude some drainage holes 147 on the outer periphery of the retention portion 154. Drainage holes 147 located on the radially inward side of the retention structure would not be appreciably occluded when such tissues contact the outer periphery of the retention portion 154. Further, risk of injury to the tissues from pinching or contact with the drainage holes 147 can be reduced or ameliorated.

In some examples, the retention portion 154 can include one or more mechanical stimulation devices for providing stimulation to nerves and muscle fibers in adjacent tissues of the ureter(s) and renal pelvis. For example, the mechanical stimulation devices can include linear or annular actuators embedded in or mounted adjacent to portions of the sidewall of the catheter tube 122 and configured to emit low levels of vibration. In some examples, mechanical stimulation can be provided to portions of the ureters and/or renal pelvis to supplement or modify therapeutic effects obtained by application of negative pressure. While not intending to be bound by theory, it is believed that such stimulation affects adjacent tissues by, for example, stimulating nerves and/or actuating peristaltic muscles associated with the ureter(s) and/or renal pelvis. Stimulation of nerves and activation of muscles may produce changes in pressure gradients or pressure levels in surrounding tissues and organs which may contribute to or, in some cases, enhance therapeutic benefits of negative pressure therapy.

In some examples, the pump module 110 further comprises an outlet line 158 extending from the pump module 110 to a portion of the patient's urinary tract 2. The outlet line 158 can formed from a similar material and have similar dimensions to the inlet line 146. The outlet line 158 may extend from the bladder, through the urethral sphincter and the urethra, and to a collection container external to the body. In some examples, the length of the outlet line 158 may range from about 30 cm to about 120 cm depending on the gender and age of the patient.

Negative Pressure Therapy System

Figure 12:
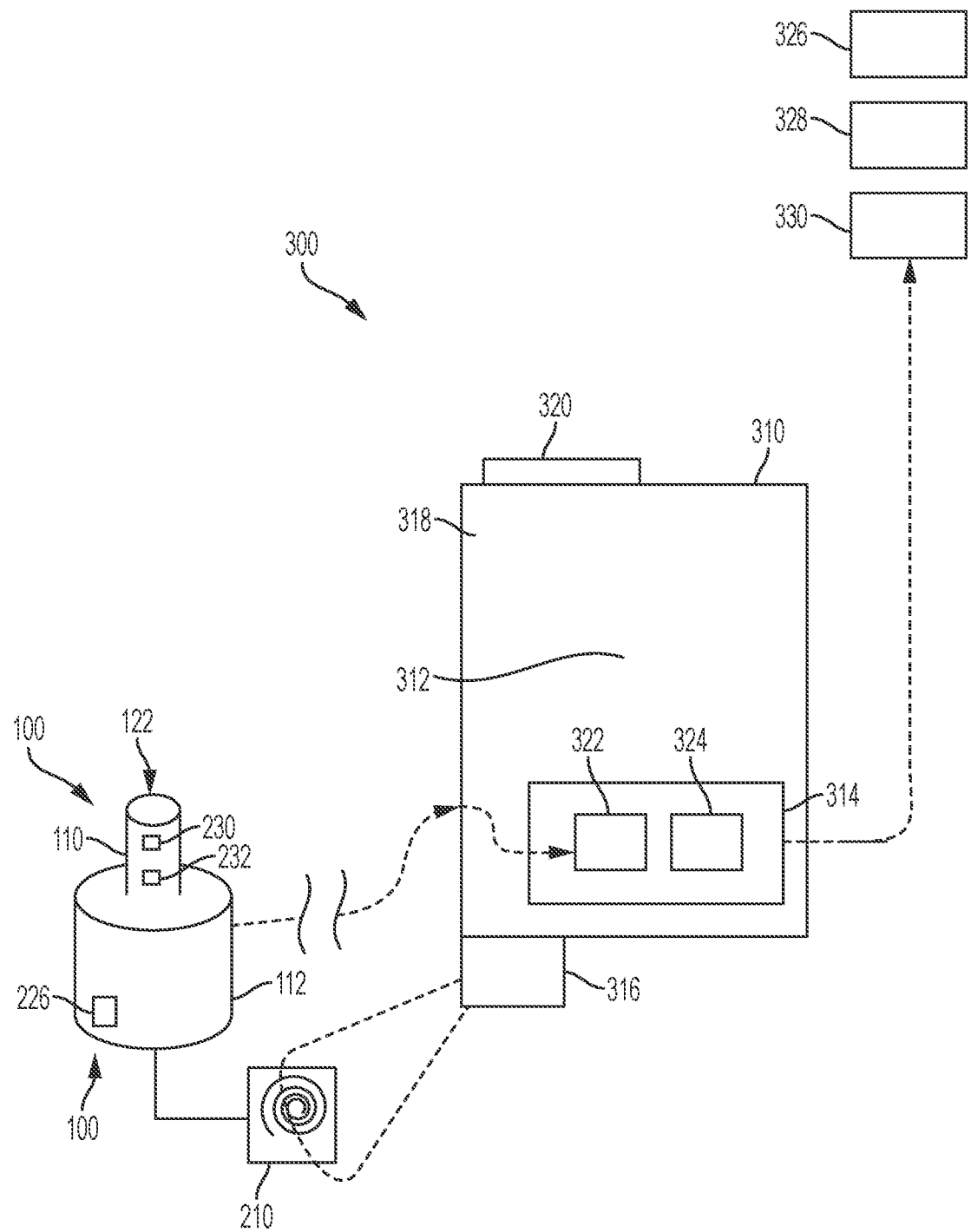
FIG. 12 is a schematic drawing of a system for inducing negative pressure in a patient's urinary tract comprising a pump assembly according to an example of the disclosure.

Referring now to FIG. 12, the pump assembly 100 can be a component of a negative pressure therapy or treatment system 300 for providing negative pressure therapy to a patient. The system 300 comprises the pump assembly 100 in communication with one or more computer devices positioned outside of the patient's body for controlling operation of the pump assembly 100 and for receiving, processing, and analyzing data generated by indwelling components of the pump assembly 100.

In some examples, as shown in FIG. 12, the system 300 comprises a remote control device 310 in wired or wireless communication with the control module 112 of the pump assembly 100. The remote control device 310 can be a dedicated electronic device configured to communicate with the pump assembly 100. In other examples, the remote control device 310 is a general purpose computer device configured to execute software for communicating with and/or controlling operation of the pump assembly 100. For example, the remote control device 310 can be a handheld web-enabled computer device, such as a smart phone, tablet PC, or personal digital assistant. In other examples, the remote control device 310 can be a laptop computer, desktop computer, or computer server as is known in the art. The remote control device 310 can be located in close proximity to the patient. For example, as previously described, the remote control device 310 can be a portable device which is placed in a pocket, fanny pack, holster, or harness worn by the patient and configured to position the remote control device 310 as close to the pump assembly 100 as possible. In other examples, the remote control device 310 may be a stationary electronic device placed, for example, in a patient's house or hospital room, and configured to communicate with the pump assembly 100 by a long-range data communications protocol, such as WiFi.

In some examples, the remote control device 310 comprises a controller 312, a communications interface 314 configured to communicate with the pump assembly 100 and with other remote computer devices or networks, and optionally an electromagnetic field generator 316 configured to generate an electromagnetic field to cause the induction coil 210 to generate power.

In some examples, the remote control device 310 further comprises a feedback and/or user interface module 318 operatively connected to a feedback device, such as a visual display 320. The feedback and/or user interface module 318 is configured to receive information generated by the one or more sensors 230, 232 associated with the pump module 110 and to provide feedback to the user about operating conditions of the pump assembly 100 and/or about a physiological condition of the patient. For example, the feedback and/or user interface module 318 may be configured to cause the visual display 320 to display information about a volume and/or flow rate of urine which passes through the flow channel 122 or about an amount of negative pressure being generated by the pump module 110. In other examples, the displayed information can also include information about the pump assembly 100, such as a charge remaining of the battery 226 or estimated time until the battery 226 will need to be recharged. In some examples, information about a treatment protocol for a patient can also be displayed. For example, information about how long negative pressure will continue to be delivered to the patient or showing a pattern of positive and negative pressures to be delivered to the patient may be displayed.

In some examples, the communications interface 314 comprises a short-range data transceiver 322 configured to communicate with the communications interface of the control module 112. For example, the short-range data transceiver 322 can comprise a Bluetooth® transceiver, near-field communications (e.g., RFID) transceiver, or similar data transmission device. Since the remote control device 310 is configured to be positioned as close to the pump assembly 100 as possible, the transmission range of the short-range data transceiver 322 need only be a few feet or less. In some examples, the communications interface 314 further comprises a long-range data transceiver 324 for transmitting information collected by the pump assembly 100 and remote control device 310 to a remote source such as a computer network 326, a database 328, or a web-based portal or website 330. For example, information about the patient and/or about treatment provided by the pump assembly 100 can be transmitted from the remote control device 310 to the remote database 328 for inclusion in the patient's electronic health record. A confirmation that treatment has been provided can also be transmitted to medical professionals such as a responsible physician. In some cases, the physician may be able to review the confirmation as well as physiological information about the patient using, for example, the web-based portal 330.

Deployment

The pump assembly 100, battery 226, and/or induction coil 220 are configured to be inserted into the bladder, ureter, and/or renal pelvis through the patient's urethra. In order to facilitate placement and deployment in this manner, the pump assembly 100 described herein is configured to fit within a deployment device, such as a catheter tube and, once advanced from the tube, is configured to automatically transition to deployed positions. In some configurations, the entire assembly, including the pump module, control module, and induction coil, can be delivered into the ureter and bladder via the urethra using, for example, a 12-16 Fr catheter (4.0-5.3 mm in outer diameter). In other examples, portions of the pump assembly can be delivered through an abdominal incision or a nephrostomy or urostomy transdermal procedure.

As shown in FIGS. 13A and 13B, an exemplary deployment catheter 410 for use with the pump assembly 100 comprises a flexible elongated tube 412 comprising an open distal end 414 configured to be inserted into the urinary tract through the urethra, a proximal end 416, which can be configured to remain outside the patient's body, and a sidewall 418, such as a substantially continuous sidewall formed from a flexible medical grade plastic material, extending therebetween. For example, the elongated tube 412 can be formed from materials including biocompatible polymers, polyvinyl chloride, polytetrafluoroethylene (PTFE) such as Teflon®, silicone coated latex, or silicone. In one example, the tube 412 is formed from a thermoplastic polyurethane. At least a portion or all of the catheter 410, such as the tube 412, can be coated with a hydrophilic coating to facilitate insertion and/or removal, and/or to enhance comfort. In some examples, the coating is a hydrophobic and/or lubricious coating. For example, suitable coatings can comprise ComfortCoat® hydrophilic coating which is available from Koninklijke DSM N.V. or hydrophilic coatings comprising polyelectrolyte(s) such as are disclosed in U.S. Pat. No. 8,512,795, which is incorporated herein by reference.

In some examples, the proximal end 416 of the tube 412 can comprise a hub (not shown) including a guidewire lumen port for assisting a user in positioning the catheter 410 through the urethra and into the bladder and/or ureter. The catheter 410 can be a standard deployment catheter formed from a biocompatible flexible material such as, for example, silicone rubber. The elongated tube 412 can be any standard size for insertion in the urinary tract, such as a 12 Fr to 16 Fr tube. The length of the elongated tube 412 may range from about 30 cm to about 120 cm depending on the gender and age of the patient.

As shown in FIGS. 13A and 13B, the pump assembly 100, including the pump module 110, control module 112, and induction coil 210, is configured to be positioned within the tube 412 in a contracted position. The pump assembly 100 is advanced through the tube 412 by a pusher rod 420, as shown in FIG. 13B. Once the open distal end 414 of the catheter 410 is advanced through the urinary tract to a desired position within the bladder, ureter, or kidney, a user may advance the pusher rod 420 through the elongated tube 412 to cause the components of the pump assembly 100 to exit the tube 412 through the open distal end 414 thereof. Once clear of the tube 412, structures of the pump module 110 and control module 112 may deploy from a contracted position to a deployed position. For example, radially extending barbs 140 (shown in FIG. 4) may extend radially outward from the sidewall 120 of the pump module 110 and come into contact with the interior ureter wall to maintain positioning of the pump module 110 within the ureter. In a similar manner, once the induction coil 210 extends past the open distal end 414 of the elongated tube 412, it may uncurl in the manner previously described. In some examples, the induction coil 210 may be biased to its uncurled state, in which case it may uncurl automatically as soon as it is removed from the elongated tube 412. In other examples, a user may manually cause the induction coil 210 to uncurl by actuating a release button or triggering wire.

In order to deploy the pump assembly 100 in a patient's urinary tract, a medical professional may first advance a guidewire to a desired position in the bladder and/or ureter. In some instances, visualization devices, such as a cystoscope, may be used to obtain visualization of the bladder and ureter openings to assist in positioning of the distal end of the guidewire. The delivery catheter 410 can be delivered over the guidewire. For example, a medical professional may insert the delivery catheter 410 over the guidewire and advance the distal end 414 of the catheter 410 over the guidewire toward the ureteral orifice 24, 26. Once the distal end 414 of the catheter 410 is in place, the medical professional can begin to push the pump assembly 100 from the elongated tube 412 by advancing the pusher rod 420 through the deployment elongated tube 412. As it is expelled from the elongated tube 412, the open distal end 118 of the pump module 110 is advanced through the ureteral orifice 24, 26 and into a distal end of the patient's ureter. The control module 112 and induction coil 220 can remain in the bladder.

In some examples, as previously discussed, housings 114, 128 of the pump module 110 and/or control module 112 can include retractable or permanently extending barbs 140, 144 for mounting the module(s) 110, 112 to a surface of the ureter, renal pelvis, bladder, or urethra. In some examples, once the pump assembly 100 comprising the pump module 110 and control module 112 is in position in the patient's urinary tract, the user may actuate a release mechanism to cause the barbs 140, 144 to extend toward the interior wall of the ureter, renal pelvis, bladder, or urethra r. In other examples, the barbs 140, 144 may extend automatically as the elongated tube is being retracted. Retraction of the elongated tube 412 also causes the deployable induction coil 210 to uncurl from a rolled configuration to a substantially flat configuration.

Bladder Pump Assembly

Figure 14:
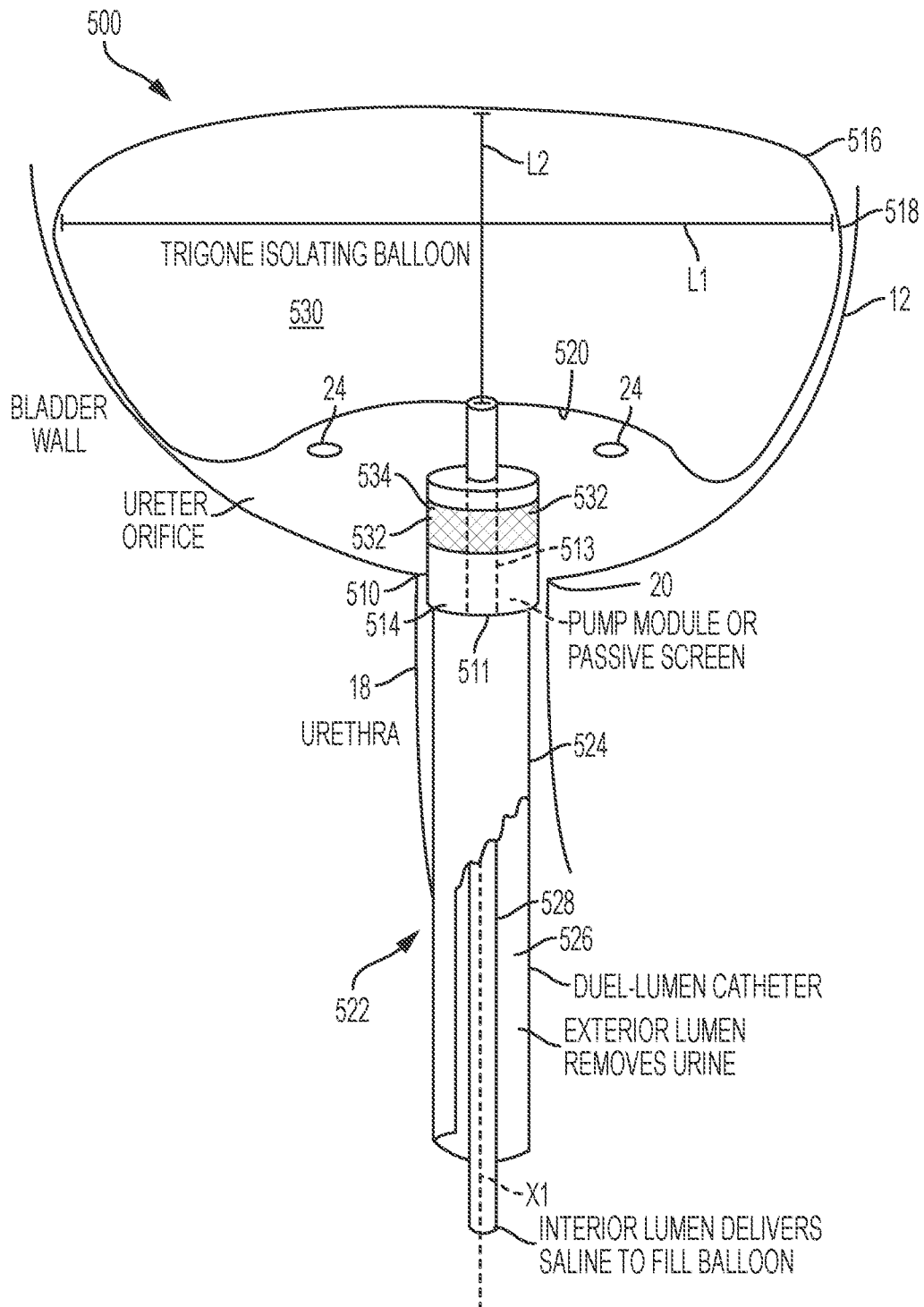
FIG. 14 is a schematic drawing of a pump assembly including a pump module positioned in a patient's bladder according to an example of the present disclosure.

According to another example of the disclosure, a bladder pump assembly 500 for inducement of negative pressure in the bladder is illustrated in FIG. 14. Negative pressure induced in the bladder also acts on the ureter and kidneys to draw urine from the kidneys. As discussed herein, such negative pressure is believed to enhance urine production resulting in physiological benefits, such as reduced venous congestion and reduced risk of acute kidney injury.

As shown in FIG. 14, the bladder pump assembly, shown generally as 500, comprises a pump module 510. The pump module 510 can be substantially similar to previously described pump modules and can include, for example, impeller or piezoelectric configurations as shown in FIGS. 7 and 8. In some examples, the pump module 510 comprises an annular housing 512 sized for placement in the patient's bladder. For example, the pump module 510 can be placed adjacent to the urethral opening or sphincter 20, such that the sphincter 20 seals about an outer circumference 514 of the housing to prevent fluid from leaking from the bladder.

In some examples, the pump module 510 comprises fluid entry holes or ports 532 extending through a sidewall 534 of the module 510 for drawing fluid into a central channel 513 of the module 510. In some examples, a diameter of each of the drainage holes or ports 532 is about 0.5 mm to 2.0 mm or about 0.75 mm to 1.0 mm. The distance between adjacent drainage holes or ports 532 about the circumference of the sidewall 534 can be about 5 mm to about 30 mm or about 10 mm to 20 mm. The holes or ports 532 can comprise a circular opening, a square shaped opening, an elliptical opening, and any combination thereof. In some examples, the holes or ports 532 can be covered by a screen or filter for preventing solid materials from being draw into the pump module 510.

The assembly 500 further comprises a bladder wall support 516 extending from the pump module 510. The bladder wall support 516 is configured to prevent a superior portion 15a of the bladder wall 15 from collapsing when negative pressure is applied to the bladder 12, ureter 8, 10, and kidneys 4, 6 by the pump module 510. In particular, the bladder wall support 516 maintains at least the superior portion 15a of the bladder 12 in an un-collapsed state in which the ureteral orifices 24, 26 are not occluded by the collapsed bladder wall 15. Exemplary bladder wall supports, which can be used in a negative pressure therapy system for providing negative pressure to portions of the urinary tract, such as the bladder, ureters, and kidneys, are described in International Publication No. WO 2017/015345 entitled "Catheter Device and Method for Inducing Negative Pressure in a Patient's Bladder", the contents of which is incorporated by reference herein in its entirety.

In some examples, the bladder wall support 516 comprises an inflatable balloon 518 configured to expand from a collapsed state to an inflated state. The balloon 518 is configured to isolate the trigone region 22 of the bladder 12 from the superior bladder wall 15a, thereby preventing the superior bladder wall 15a from collapsing into the trigone region 22 when negative pressure is applied thereto. In some examples, the balloon 518 can be about 1.0 cm to 2.3 cm in diameter, and preferably about 1.9 cm (0.75 in) in diameter. The balloon 518 is preferably formed from a flexible material including, for example, biocompatible polymers, polyvinyl chloride, polytetrafluoroethylene (PTFE) such as Teflon®, silicone coated latex, or silicone.

As shown in FIG. 14, in some examples, the balloon 518 has a substantially flattened or elongated cross section having a maximum inflated width L1 of, for example, about 15 cm or less or about 10 cm or less, which is greater than its maximum inflated height L2 of, for example, about 5 cm or less or 2.5 cm or less. The width L1 generally corresponds to the width of a patient's bladder. In some examples, a bottom or proximal surface 520 of the balloon 518 is a concave surface offset from the proximal surface of the bladder by about 1 cm to about 3 cm so as to permit free flow of urine from the ureter orifice 24.

The pump assembly 500 further comprises a drainage conduit or tube 522 comprising an elongated tubular member 524. As previously described, a tubular member for insertion in the urinary system, such as tubular member 524, can be formed from any suitable flexible material including biocompatible polymers, polyvinyl chloride, polytetrafluoroethylene (PTFE) such as Teflon®, silicone coated latex, or silicone. In some examples, at least a portion or all of the tubular member can be coated with a hydrophilic coating to facilitate insertion and/or removal and/or to enhance comfort. In some examples, the coating is a hydrophobic and/or lubricious coating. For example, a suitable coating can comprise ComfortCoat® hydrophilic coating.

In some examples, the elongated tubular member 524 extends from a proximal end 511 of the pump module 510, through the urethra 18, and extends to the outside of the patient's body. The drainage catheter 522 may be connected to a fluid collection container, such as a urine collection bag or pouch (not shown). The drainage catheter 522 can be a single or multi-lumen catheter comprising one or more drainage lumens 526 in fluid communication with the channel 513 of the pump module 510. In some examples, the drainage catheter 522 further comprises an inflation lumen 528 in fluid communication with an interior 530 of the inflatable balloon 518. As shown in FIG. 14, in some examples, the inflation lumen 528 extends through the pump module 510 and into the interior 530 of the balloon 518. The inflation lumen 528 is used to deliver a filling material, such as saline solution, to inflate the balloon 518. When a user is prepared to remove the pump assembly 500 from the body, the balloon 518 can be deflated by emptying the filling material, such as saline solution contained in the balloon interior 520, through the inflation lumen 528 and out of the body.

In some examples, the inflation lumen 528 extends through the drainage lumen 526, as shown in FIG. 14. For example, the inflation lumen 528 may extend through the drainage lumen 526 such that a longitudinal central axis X1 of the drainage lumen 526 is substantially co-extensive with a longitudinal central axis of the inflation lumen 528. However, many different arrangements of the drainage lumen 526 and inflation lumen 528 may be used within the scope of the present disclosure. For example, a separate drainage lumen 526 and inflation lumen 528 may extend through the drainage catheter 522 in a side-by-side configuration. Other configurations of the drainage lumen 526 and inflation lumen 528 will also be apparent to those of ordinary skill in the art.

In use, the bladder pump assembly 500 comprising the pump module 510, bladder wall support 516, and elongated tubular member 524 is advanced through the urethra 18 into the bladder 12. The balloon 518 of the bladder wall support 516 is then expanded within the bladder 12 as shown in FIG. 14. Once the elongated member 524 and pump module 510 are in place, the urethral sphincter 20 can be permitted to seal or partially seal around the outer circumference 514 of the pump module 510. Once the balloon 518 and pump module 510 are positioned within the bladder 12, a user may actuate a pump element of the pump module 510 to draw urine from the bladder 12 into the pump module 510 through the fluid entry ports 532. The negative pressure generated by the pump module 510 also acts on more distal portions of the urinary tract. For example, the ureter(s) and kidney(s) can be exposed to the negative pressure to increase renal perfusion in the manner described herein. When the pump module 510 is actuated, fluid is drawn through the channel 513 of the pump module 510 due to motion of the pump element and expelled from the pump module 510 to the drainage lumen 526 of the drainage catheter 522. The collected fluid drains from the body through the drainage catheter 522 where it is collected in a fluid collection container, such as a bag or pouch, located outside the patient's body. Collected urine can be analyzed to monitor patient physiological condition and to confirm that the pump assembly 510 is operating and providing negative pressure in an expected manner. The pump module 510 can further comprise sensors 230, 232, such as are discussed above to monitor pump performance and/or physiological conditions as desired.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. A pump assembly comprising:
   (a) a pump module comprising:
      a housing comprising an open proximal end, an open distal end, and a sidewall extending therebetween defining a flow channel within the housing, wherein the entire housing is positioned within at least one of the interior portion of the ureter, the interior portion of the renal pelvis, the interior portion of the bladder, or the interior portion of the urethra of the patient; and
      a pump mechanism positioned entirely within the housing, and being configured to draw fluid through the flow channel of the housing between the open distal end and the open proximal end of the housing; and
   (b) a control module coupled to the pump module, the control module being configured to actuate and direct motion of the pump mechanism to propel fluid through the flow channel and to control flow rate of the fluid passing through the flow channel.

2. The pump assembly of claim 1, wherein the control module further comprises a control module housing, and wherein a maximum outer diameter of the pump module housing is less than a maximum outer diameter of the control module housing.

3. The pump assembly of claim 2, wherein the maximum outer diameter of the pump module housing is about 0.5 mm to about 5.0 mm.

4. The pump assembly of claim 1, wherein the control module further comprises a control module housing having a maximum outer diameter which is larger than an interior diameter of a ureter, such that the control module does not pass from the bladder into the ureter.

5. The pump assembly of claim 1, wherein the pump module housing comprises one or more retention members extending from the sidewall for releasably attaching a portion of the pump module housing to at least one of the interior portion of the ureter, the interior portion of the renal pelvis, the interior portion of the bladder, or the interior portion of the urethra.

6. The pump assembly of claim 5, wherein the retention members are retractable to permit removal of the pump module from the ureter, renal pelvis or the bladder.

7. The pump assembly of claim 5, wherein the retention members have a length when extended of less than about 3 mm.

8. The pump assembly of claim 1, wherein the control module further comprises a control module housing comprising one or more retention members extending therefrom for releasably attaching the control module housing to an interior portion of the bladder.

9. The pump assembly of claim 1, wherein at least a portion of the pump module housing comprises a drainage channel comprising a distal portion configured to be positioned within at least one of a distal interior portion of the ureter and/or the interior portion of the renal pelvis.

10. The pump assembly of claim 9, wherein the drainage channel is formed integrally with the pump module housing or as a separate tube or conduit in fluid connection with the open distal end of the pump module housing.

11. The pump assembly of claim 9, wherein the distal portion of the drainage channel comprises a coil.

12. The pump assembly of claim 11, wherein the coil comprises one or more perforations in a sidewall of the coil.

13. The pump assembly of claim 11, wherein the coil comprises one or more perforations in an inwardly facing side of a sidewall of the coil.

14. The pump assembly of claim 2, wherein the pump module housing is integrally formed with or connected to the control module housing.

15. The pump assembly of claim 1, wherein the control module further comprises a control module housing comprising a generally cylindrical housing comprising an open distal end connected to the open proximal end of the pump module housing, an open proximal end, and a flow channel in fluid communication with the flow channel of the pump module housing and extending between the proximal end and the distal end of the control module housing.

16. The pump assembly of claim 1, wherein the control module further comprises a control module housing which is separate from the pump module housing and wherein electronic circuitry of the control module is operatively connected to the pump module via a wired or wireless connection.

17. The pump assembly of claim 1, wherein the pump mechanism comprises an impeller positioned within the flow channel of the pump module housing which rotates to draw fluid through the channel.

18. The pump assembly of claim 1, wherein the pump mechanism comprises a piezoelectric diaphragm positioned within the channel that can be configured to alternately extend from and retract to an inner surface of the sidewall to draw fluid through the flow channel.

19. The pump assembly of claim 18, wherein the pump module further comprises a distal valve positioned in a portion of the flow channel distal to the pump mechanism and a proximal valve positioned in a portion of the flow channel proximal to the pump mechanism.

20. The pump assembly of claim 19, wherein the distal valve and the proximal valve each comprise a one-way check valve configured to produce one-directional flow of fluid through the flow channel from the distal end to the proximal end thereof.

21. The pump assembly of claim 1, wherein the pump module is configured to provide negative pressure ranging from about 0 mmHg to about 150 mmHg.

22. The pump assembly of claim 1, wherein the pump module is configured to produce a negative pressure in the ureter sufficient for establishing a pressure gradient across filtration anatomy of a kidney to facilitate urine flow towards the ureter.

23. The pump assembly of claim 1, further comprising a battery positioned in at least one of a control module housing or the pump module housing for providing power to at least one of the control module or pump mechanism.

24. The pump assembly of claim 23, wherein the battery is rechargeable.

25. The pump assembly of claim 1, wherein the control module comprises a wireless transceiver configured to receive operating instructions from a remote device and to provide information about negative pressure treatment from the control module to the remote device.

26. The pump assembly of claim 1, further comprising an induction coil electronically coupled to at least one of the pump module or the control module for providing power thereto, the induction coil being configured to generate power when exposed to an electromagnetic field generated by a remote device positioned outside or within a body.

27. The pump assembly of claim 26, wherein the induction coil comprises a conductive wire at least partially disposed on a flexible substrate.

28. The pump assembly of claim 27, wherein the flexible substrate is transitionable from a rolled configuration in which the flexible substrate is rolled about a central axis thereof to a size suitable for delivery through a catheter to a deployed configuration in which the flexible substrate is at least partially unrolled from the rolled configuration.

29. The pump assembly of claim 26, further comprising a battery electronically coupled to the induction coil, the battery being configured to be recharged by power produced by the induction coil.

30. A pump assembly for inducement of negative pressure in a bladder, the assembly comprising:
  a pump module positioned in a portion of a bladder, the pump module comprising a housing comprising an open proximal end, an open distal end, and a sidewall extending therebetween, the housing defining a flow channel within the housing for conducting fluid through an interior portion of the bladder, and a pump mechanism positioned within the flow channel of the housing and being configured to propel fluid through the flow channel of the housing;
  a bladder wall support for maintaining at least a portion of the bladder wall in an un-collapsed state in which ureter orifices are not occluded by the bladder wall; and
  a drainage catheter extending from the proximal end of the pump module through the urethra and from the body, the drainage catheter comprising a drainage lumen in fluid communication with the flow channel of the housing of the pump module for directing fluid expelled from the pump module from the body.

31. The pump assembly of claim 30, wherein the bladder wall support comprises an inflatable trigone isolating balloon, comprising a superior surface portion for supporting a superior wall of the bladder and a concave inferior surface portion.

32. The pump assembly of claim 31, wherein the trigone isolating balloon has a maximum height of about 5 cm and a maximum outer diameter of about 15 cm.

33. The pump assembly of claim 31, wherein the drainage catheter further comprises an inflation lumen in fluid communication with an interior of the trigone isolating balloon for providing fluid to an interior of the trigone isolating balloon to inflate the balloon.

34. The pump assembly of claim 33, wherein the inflation lumen extends through the drainage lumen, such that a longitudinal central axis of the drainage lumen is substantially co-extensive with a longitudinal central axis of the inflation lumen.

35. The pump assembly of claim 30, wherein the pump module housing further comprises a plurality of drainage openings extending therethrough for drawing fluid from the bladder into the flow channel.

36. The pump assembly of claim 30, wherein the pump module further comprises an annular filter extending about at least a portion of the housing sidewall and covering one or more of the plurality of drainage openings for filtering fluid as the fluid is drawn into the flow channel.

37. A pump assembly comprising:
  (a) a pump module comprising:
    a housing comprising an open proximal end, an open distal end, and a sidewall extending therebetween defining a flow channel within the housing, wherein the entire housing is positioned within at least one of the distal interior portion of the ureter or the interior portion of the renal pelvis;

a pump mechanism positioned entirely within the housing, and being configured to draw fluid through the flow channel of the housing between the open distal end and the open proximal end of the housing; and (b) a control module coupled to the pump module, the control module being configured to actuate and direct motion of the pump mechanism to propel fluid through the flow channel and to control flow rate of the fluid passing through the flow channel, wherein the flow channel is formed integrally with the pump module housing or as a separate tube or conduit in fluid connection with the open distal end of the pump module housing.

38. A system for providing negative pressure therapy to a ureter and/or kidney, the system comprising:

a pump assembly, comprising:

(a) a pump module comprising:

a housing comprising an open proximal end, an open distal end, and a sidewall extending therebetween defining a flow channel within the housing, wherein the entire housing is positioned within at least one of the interior portion of the ureter, the interior portion of the renal pelvis, the interior portion of the bladder, or the interior portion of the urethra; and a pump mechanism positioned entirely within the housing, and being configured to draw fluid through the flow channel of the housing between the open distal end and the open proximal end of the housing; and (b) a control module coupled to the pump module, the control module being configured to actuate and direct motion of the pump mechanism to propel fluid through the flow channel and to control flow rate of fluid passing through the flow channel;

a power supply for providing power to the pump assembly; and a remote control device in wired or wireless communication with the control module, the remote control device being configured to provide instructions to the control module for operating the pump assembly and to receive information from the control module about at least one of the pump module or a body.

39. The system of claim 38, wherein the control module further comprises a control module housing, and wherein a maximum outer diameter of the pump module housing is less than a maximum outer diameter of the control module.

40. The system of claim 38, wherein the control module is sized for insertion into the bladder.

41. The system of claim 38, wherein the power supply is a battery.

42. The system of claim 38, wherein the power supply is an induction coil.

43. The system of claim 42, wherein the remote control device further comprises an electromagnetic field generator configured to generate an electromagnetic field which, when exposed to the induction coil, causes the induction coil to generate power for operating at least one of the control module or the pump module.

44. The system of claim 42, wherein the power supply further comprises a battery electronically coupled to the induction coil, the battery being configured to be recharged by power produced by the induction coil.

45. The system of claim 44, wherein information received from the control device comprises at least one of an indication that the battery is being recharged by the induction coil, an indication that the battery is fully charged, or an indication of a charge remaining of the battery.

46. The system of claim 38, further comprising a remote database comprising electronic health records, and wherein the remote control device is configured to wirelessly transmit information about or from the health records to the remote database.

47. The system of claim 38, further comprising one or more sensor(s) in fluid communication with the flow channel of the pump module housing, the sensor(s) being configured to measure a pump operating parameter or a physiological condition based on sensed information about fluid passing through the flow channel.

48. The system of claim 38, wherein the remote control device further comprises a display, and wherein the remote control device is configured to display the information received from the control module about at least one of the pump module or the body on the display.

49. A method for providing negative pressure therapy to a portion of the urinary tract, the method comprising:

positioning a pump assembly comprising:

(a) a pump module comprising:

a housing comprising an open proximal end, an open distal end, and a sidewall extending therebetween defining a flow channel within the housing, wherein the entire housing is positioned within at least one of the interior portion of the ureter, the interior portion of the renal pelvis, the interior portion of the bladder, or the interior portion of the urethra; and a pump mechanism positioned entirely within the housing, and being configured to draw fluid through the flow channel of the housing between the open distal end and the open proximal end of the housing; and (b) a control module coupled to the pump module, the control module being configured to actuate and direct motion of the pump mechanism to propel fluid through the flow channel and to control flow rate of the fluid passing through the flow channel; and actuating the pump mechanism thereby causing the pump mechanism to propel fluid through the flow channel thereof to deliver negative pressure to a portion of the urinary tract.

50. The method of claim 49, wherein the control module further comprises a control module housing sized for insertion in the bladder, and wherein a maximum external diameter of the pump module is less than the maximum outer diameter of the control module.

51. The method of claim 49, wherein the assembly is deployed within a portion of the bladder, renal pelvis, urethra, and/or ureter by use of a catheter.

52. The method of claim 49, wherein positioning the pump assembly further comprises deploying retention barbs against an inner wall of the bladder, renal pelvis, urethra, and/or ureter to maintain positioning of the pump assembly within the bladder and/or ureter.

53. The method of claim 49, wherein negative pressure is delivered in a range of between 0 and about 150 mmHg.

54. The method of claim 49, wherein activating the pump module further comprises periodically reversing pump direction for a period of time to provide intermittent positive pressure to the urinary tract.

55. The pump assembly of claim 1, wherein at least a portion of the pump module is configured to be positioned within at least one of an interior portion of a ureter, an interior portion of a renal pelvis, an interior portion of a bladder, or an interior portion of a urethra for providing negative pressure to at least one of the ureter or kidney.

56. The pump assembly of claim 1, wherein the flow channel conducts fluid through at least one of the interior portion of the ureter, the interior portion of the renal pelvis, the interior portion of the bladder, or the interior portion of the urethra.

57. A negative pressure therapy system for increasing urine production, the negative pressure therapy system comprising:
(a) a pump assembly, the pump assembly comprising:
  (i) a pump module comprising:
    a housing comprising an open proximal end, an open distal end, and a sidewall extending therebetween defining a flow channel within the housing, wherein the entire housing is positioned within at least one of the interior portion of the ureter, the interior portion of the renal pelvis, the interior portion of the bladder, or the interior portion of the urethra of the patient; and
    a pump mechanism positioned entirely within the housing, and being configured to draw fluid through the flow channel of the housing between the open distal end and the open proximal end of the housing; and
  (ii) a control module coupled to the pump module, the control module being configured to actuate and direct motion of the pump mechanism to propel fluid through the flow channel and to control flow rate of the fluid passing through the flow channel; and
(b) a catheter having (i) a proximal portion including a drainage lumen and (ii) a distal portion comprising a retention portion comprising one or more drainage ports that permit fluid flow into the drainage lumen, wherein the proximal portion of the catheter is configured to be connected to the pump to provide negative pressure through the catheter to the kidney.

58. The negative pressure therapy system of claim 57, wherein the retention portion comprises a radially inwardly facing side comprising the one or more drainage ports, and a radially outwardly facing side that is essentially free of drainage ports.

59. The pump assembly of claim 1, wherein the pump assembly is configured to be deployed in a urinary tract of a patient.

60. The pump assembly of claim 59, wherein the patient is a human.

61. The pump assembly of claim 59, wherein the patient is an animal.

62. The pump assembly of claim 59, wherein the patient is a dog.

63. The pump assembly of claim 37, wherein the pump assembly is configured to be deployed in a urinary tract of a patient.

64. The pump assembly of claim 63, wherein the patient is a human, an animal, or a dog.

65. The system of claim 38, wherein the system is configured to be deployed in a urinary tract of a patient.

66. The system of claim 65, wherein the patient is a human, an animal, or a dog.

67. The method of claim 49, wherein the pump assembly is configured to be deployed in a urinary tract of a patient.

68. The method of claim 67, wherein the patient is a human, an animal, or a dog.

69. The system of claim 57, wherein the system is configured to be deployed in a urinary tract of a patient.

70. The system of claim 69, wherein the patient is a human, an animal, or a dog.

71. The pump assembly of claim 37, wherein the pump mechanism comprises an impeller positioned within the flow channel of the pump module housing which rotates to draw fluid through the channel.

72. The pump assembly of claim 37, wherein the pump mechanism comprises a piezoelectric diaphragm positioned within the channel that can be configured to alternately extend from and retract to an inner surface of the sidewall to draw fluid through the flow channel.

73. The pump assembly of claim 38, wherein the pump mechanism comprises an impeller positioned within the flow channel of the pump module housing which rotates to draw fluid through the channel.

74. The pump assembly of claim 38, wherein the pump mechanism comprises a piezoelectric diaphragm positioned within the channel that can be configured to alternately extend from and retract to an inner surface of the sidewall to draw fluid through the flow channel.

75. The pump assembly of claim 49, wherein the pump mechanism comprises an impeller positioned within the flow channel of the pump module housing which rotates to draw fluid through the channel.

76. The pump assembly of claim 49, wherein the pump mechanism comprises a piezoelectric diaphragm positioned within the channel that can be configured to alternately extend from and retract to an inner surface of the sidewall to draw fluid through the flow channel.

77. The pump assembly of claim 57, wherein the pump mechanism comprises an impeller positioned within the flow channel of the pump module housing which rotates to draw fluid through the channel.

78. The pump assembly of claim 57, wherein the pump mechanism comprises a piezoelectric diaphragm positioned within the channel that can be configured to alternately extend from and retract to an inner surface of the sidewall to draw fluid through the flow channel.

79. The pump assembly of claim 18, wherein the piezoelectric diaphragm is a flexible conductive film.

80. The pump assembly of claim 72, wherein the piezoelectric diaphragm is a flexible conductive film.

81. The pump assembly of claim 74, wherein the piezoelectric diaphragm is a flexible conductive film.

82. The pump assembly of claim 76, wherein the piezoelectric diaphragm is a flexible conductive film.

83. The pump assembly of claim 78, wherein the piezoelectric diaphragm is a flexible conductive film.

* * * * *

UNITED STATES PATENT AND TRADEMARK OFFICE
CERTIFICATE OF CORRECTION

| | | |
|---|---|---|
| PATENT NO. | : 12,059,543 B2 | |
| APPLICATION NO. | : 16/640210 | |
| DATED | : August 13, 2024 | |
| INVENTOR(S) | : David E. Orr et al. | |

It is certified that error appears in the above-identified patent and that said Letters Patent is hereby corrected as shown below:

On the Title Page

Column 2, item (57) Abstract, Line 7, delete "and/the" and insert -- and/or the --

In the Claims

Column 36, Line 16, Claim 1, after "is" insert -- configured to be --

Column 38, Line 19, Claim 30, after "module" insert -- configured to be --

Column 39, Line 2, Claim 37, after "is" insert -- configured to be --

Column 39, Line 25, Claim 38, after "is" insert -- configured to be --

Column 40, Line 28, Claim 49, after "is" insert -- configured to be --

Column 41, Line 16, Claim 57, after "is" insert -- configured to be --

Signed and Sealed this
Twenty-second Day of October, 2024

Katherine Kelly Vidal
*Director of the United States Patent and Trademark Office*